US007354646B2

(12) United States Patent
Himori et al.

(10) Patent No.: US 7,354,646 B2
(45) Date of Patent: Apr. 8, 2008

(54) WATER-ABSORBENT POLYMER COMPOSITE COMPRISING TWO OR MORE FIBERS, AND COMPOSITION THEREOF

(75) Inventors: Shunichi Himori, Yokkaichi (JP); Kiichi Itoh, Yokkaichi (JP); Yoshiaki Mori, Yokkaichi (JP); Yasunari Sugyo, Yokkaichi (JP); Taisuke Ishii, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 64 days.

(21) Appl. No.: 11/248,191

(22) Filed: Oct. 13, 2005

(65) Prior Publication Data

US 2006/0081812 A1    Apr. 20, 2006

Related U.S. Application Data

(63) Continuation of application No. PCT/JP2004/005396, filed on Apr. 15, 2004.

(30) Foreign Application Priority Data

Apr. 15, 2003    (JP) .............................. 2003-110863

(51) Int. Cl.
*B32B 5/16* (2006.01)
*D02J 3/18* (2006.01)

(52) U.S. Cl. .................. 428/403; 428/375; 428/377; 428/393; 428/400; 428/401; 428/407

(58) Field of Classification Search ................ 428/403, 428/407, 372, 375, 377, 401, 400
See application file for complete search history.

(56) References Cited

U.S. PATENT DOCUMENTS

5,800,418 A * 9/1998 Ahr ............................ 604/368

FOREIGN PATENT DOCUMENTS

| JP | 61-275355 A | 12/1986 |
|----|-------------|---------|
| JP | 63-63723 A | 3/1988 |
| JP | 10-113556 A | 5/1998 |
| JP | 11-93073 A | 4/1999 |
| JP | 2000-198805 | * 7/2000 |
| JP | 2002-275760 A | 9/2002 |
| JP | 2002-370025 A | 12/2002 |
| JP | 2003-011118 | * 1/2003 |

* cited by examiner

*Primary Examiner*—H. T Le
(74) *Attorney, Agent, or Firm*—Birch, Stewart, Kolasch & Birch, LLP

(57) ABSTRACT

Disclosed is a water-absorbent polymer composite and composition thereof comprising a water-absorbent polymer particle and two or more fibers, wherein said polymer particle has a substantially spherical shape, at least one of said two or more fibers is partially wrapped in the polymer particle and partially exposed to outside the particle, and at least one of said two or more fibers is unwrapped in the polymer particle and partially adhered to a surface of the polymer particle. This water-absorbent polymer composite is characterized in that the fibers are stably fixed to the water-absorbent polymer not only in dry but also in wet through water absorption for swelling, the water-absorbent polymer content can be enlarged relative to the fibers, the polymer can be uniformly fixed to the fibers, the composite is flexible and can be thinned, opened and mixed with any other material uniformly.

19 Claims, 12 Drawing Sheets sketch

Picture101 (appearance)

fiber water-absorbent polymer

Picture102 (section)

fiber water-absorbent polymer

Picture101 (appearance)

sketch

Picture102 (section)

Picture 103 (appearance)

Picture 104 (section)

Picture105 (appearance)

fiber water-absorbent polymer

Picture106 (section)

fiber water-absorbent polymer

Picture 107 (appearance)

Picture 108 (section)

sketch fiber water-absorbent polymer

Picture109 (appearance)

fiber water-absorbent polymer

Picture110 (section)

fiber water-absorbent polymer sketch fiber
water-absorbent polymer

Picture111 (appearance)

fiber
water-absorbent polymer

Picture112 (section)

water-absorbent polymer
fiber

Picture113 (appearance)

sketch fiber water-absorbent polymer

Picture114 (section)

fiber void water-absorbent polymer

Picture115 (appearance)

sketch

— fiber

— water-absorbent polymer

Picture116 (section)

— fiber

— water-absorbent polymer

WATER-ABSORBENT POLYMER COMPOSITE COMPRISING TWO OR MORE FIBERS, AND COMPOSITION THEREOF

The present application is a continuation of PCT/JP2004/005396 with a filing date of Apr. 15, 2004, which claims the priority from Japanese Patent Application No. 110863/2003 filed on Apr. 15, 2003.

BACKGROUND OF THE INVENTION

1. Field of the Invention

The present invention relates to a water-absorbent polymer composite and a composition comprising the composite. The water-absorbent composite composition of the invention is thin and pliable and can be opened. The water-absorbent polymer composite and its composition of the invention are favorable for producing sanitary goods such as paper diapers, sanitary napkins, and other water-absorbent articles such as industrial materials.

2. Description of the Related Art

Heretofore water-absorbent polymers capable of absorbing a large amount of water have been widely used for sanitary goods, industrial materials, etc. In case where a water-absorbent polymer is combined with any other material to form its composite as in paper diapers, it is desired that the polymer is well fixed to the material before and after water absorption, the composite is thin and pliable, and the polymer content of the composite is high.

JP-A 63-63723 discloses a composite that comprises a hydrophilic substrate with fibers at least partially wrapped therein, and this is produced by kneading and dispersing hydrophilic fibers with a water-absorbent polymer wetted and swollen with water or a water-containing solvent followed by drying and grinding the resulting dispersion, or by polymerizing a water-soluble ethylenic unsaturated monomer while mixed with hydrophilic fibers followed by drying and grinding the resulting polymer mixture. The process disclosed gives a composite that comprises a water-absorbent polymer and fibers. However, the composite obtained according to the process must be ground before use. This inevitably gives broken or pulverized fiber pieces, and is therefore problematic in that fiber debris and fine water-absorbent polymer particles are formed and the non-fixed water-absorbent polymer is released. Another problem is that the molecular chains of the water-absorbent polymer are cut by mechanical shock during the kneading and dispersing operation and the water-absorbing capacity of the composite is therefore inevitably lowered. Still another problem is that, while the components are kneaded and dispersed, air is led into the resulting dispersion to form voids inside the water-absorbent polymer, and, as a result, the reduction in the water-absorbing capacity under pressure of the composite and the reduction in the bulk density thereof are also inevitable. In addition, in the composite produced according to the process, the fibers are always at least partially wrapped in the water-absorbent polymer, or that is, the process could not give a composite comprising fibers partially adhered to the surface of a water-absorbent polymer as in the present invention.

JP-B 5-58030 discloses a water-absorbent article which comprises a fibrous substrate at least partially composed of hydrophobic fibers and a water-absorbent polymer adhering to the substrate. The water-absorbent article is characterized in that at least a part of the water-absorbent polymer is nearly spherical to wrap the substrate fiber and discontinuously adheres to the substrate. Since the substrate is fibrous, the technique ensures the pliability of the composite. In addition, the water-absorbent polymer is fixed to the substrate. However, since the water-absorbent polymer wraps the fibers therein, it is inevitable that the fibers interfere with the swelling of the water-absorbent polymer. In addition, since the water-absorbent polymer is discontinuously adhered to the fibers, the ratio of water-absorbent polymer/fibers must be small. Naturally, even though a water-absorbent polymer discontinuously adheres to a fiber, the fiber may interfere with the polymer swelling when the polymer-to-polymer distance is narrow. In view of this, the ratio of water-absorbent polymer/fibers could not be enlarged. Still another problem with the technique disclosed is that the substrate usable therein is limited to hydrophobic fibers for the morphology control of the water-absorbent polymer.

JP-A 11-93073 discloses a polymer-fiber composite in which a nearly spherical water-absorbent polymer is discontinuously fixed on the surfaces of nonfabricated fibers and the non-fabricated fibers are accumulated, or the nonfabricated fibers bond to each other via the water-absorbent polymer. Naturally from the point of view that the water-absorbent polymer adheres to the fibers, it may be said that the fixation of the water-absorbent polymer is realized. However, since the water-absorbent polymer adheres to the surfaces of the fibers, the adhesion morphology is inevitably limited to point adhesion or line adhesion, and the adhesion strength in dry will be unsatisfactory. This causes a problem in that the fixation retention in dry is unsatisfactory. Still another problem is that, when the water-absorbent polymer has absorbed water and its surface is swollen and elongated, it readily peels off and moves away.

The patent publication describes an embodiment of fibers wrapped in a water-absorbent polymer. However, like in the above-mentioned JP-B 5-58030, this is defective in that the swelling retardation of the water-absorbent polymer by the fibers is inevitable. Moreover, since the fibers bonds to each other via the water-absorbent polymer, the composite is difficult to be opened. If it is forcedly opened, the water-absorbent polymer itself therein will be damaged, therefore causing a problem in that the water absorbency of the composite will lower and a non-fixed water-absorbent polymer will be released. For these reasons, it is difficult to open the composite and uniformly mix it with any other material.

SUMMARY OF THE INVENTION

The present invention has been made to solve the problems with the related art described in the above-mentioned patent publications. Specifically, the object of the invention is to provide a composition that contains a composite of a water-absorbent polymer with fibers wherein the fibers are stably fixed to the water-absorbent polymer not only in dry but also in wet through water absorption for swelling, the water-absorbent polymer content can be enlarged relative to the fibers, the polymer can be uniformly fixed to the fibers, the composite is pliable and can be thinned, opened and mixed with any other material uniformly.

The present inventors have assiduously studied and have found that the object can be attained by the invention described hereinunder.

The invention provides a water-absorbent polymer composite comprising a water-absorbent polymer particle and two or more fibers, wherein said polymer particle has a substantially spherical shape, at least one of said two or more fibers is partially wrapped in the polymer particle and partially exposed to outside the particle, and at least one of said two or more fibers is unwrapped in the polymer particle and partially adhered to a surface of the polymer particle. The invention also provides a water-absorbent composite composition comprising the water-absorbent polymer composite.

The present invention provides a composite of a water-absorbent polymer with fibers wherein the fibers are stably fixed to the water-absorbent polymer not only in dry but also in wet through water absorption for swelling, the water-absorbent polymer content can be enlarged relative to the fibers, the polymer can be uniformly fixed to the fibers, the composite is pliable and can be thinned, opened and mixed with any other material uniformly.

Figure 1:
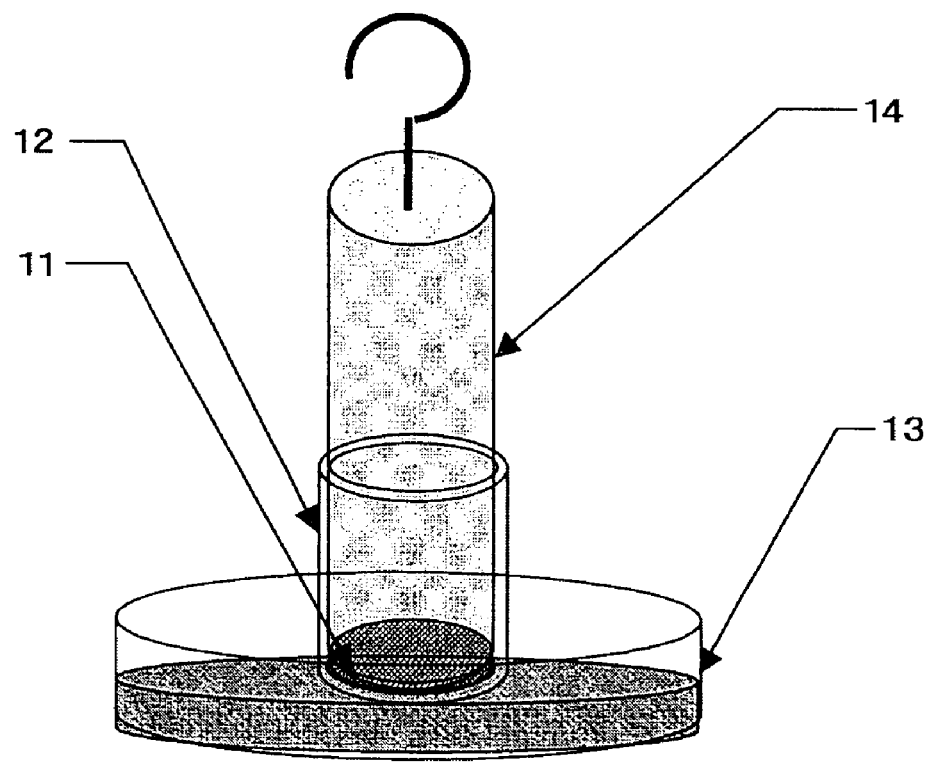
FIG. 1 is a schematic sectional view showing an instrument for water-absorbing capacity under pressure.

In these figures, there are shown adapter 1, sample stand 2, sample 3, distance 4, metal gauze 11, cylinder 12, dish 13, weight 14, water-impervious polyethylene sheet 21, Tissue 22, high-density water-absorbent polymer composite composition 24, tissue 25, water-pervious polyester fiber nonwoven fabric 26, water-absorbent article 31, cylinder 32, through-holes 33, acrylic plate 34, center 41, cutting line 42, gripper 51 and sample 52.

BEST MODE FOR CARRYING OUT THE INVENTION

The water-absorbent polymer composite and its composition of the invention are described in detail hereinunder with reference to some preferred embodiments thereof. In this description, the numerical range expressed by the wording "a number to another number" means the range that falls between the former number indicating the lowermost limit of the range and the latter number indicating the uppermost limit thereof, and these numbers are included in the range.

The water-absorbent polymer composite of the invention (hereinafter referred to as "composite A") has the structure mentioned below and comprises the constitutive elements also mentioned below. The water-absorbent polymer composite composition of the invention (hereinafter referred to as "composition of the invention") comprises the composite A as the indispensable constitutive element thereof.

I. Composite A

1. Structure and Constitutive Elements

The composite A comprises one nearly spherical, water-absorbent polymer particle and two or more fibers. At least one fiber in the composite A is partially wrapped in the water-absorbent polymer particle and partially exposed outside it. At least one fiber in the composite A is unwrapped in the water-absorbent polymer particle and partially adheres to the surface of the polymer particle. Specifically, the indispensable constitutive elements of the composite A are the following three:

<1> water-absorbent polymer particle,

<2> fiber partially wrapped in the water-absorbent polymer particle and partially exposed outside it (hereinafter referred to as "partially-wrapped fiber"), and <3> fiber adhering to the surface of the water-absorbent polymer particle but unwrapped in the particle (hereinafter referred to as "surface-adhering fiber").

The fibers that bond to the water-absorbent polymer particle in the composite A, that is, the partially-wrapped fiber <2> and the surface-adhering fiber <3> may be generically referred to as "bonding fibers". In the composite A, the dry weight ratio of the bonding fibers to the water-absorbent polymer particle is preferably in the range of 1:1 to 1:1,000, 000, more preferably 1:2 to 1:100,000, still more preferably 1:3 to 1:10,000.

2. Constitutive Elements

1) Water-absorbent Polymer

In the composite A, the water-absorbent polymer fills the role of absorbing fluid such as water, urine, blood or menstrual discharge in accordance with the use and the object of the composite A.

(Chemical Composition)

The water-absorbent polymer in the composite A is a polymer generally capable of absorbing fluid such as water, urine, blood or menstrual discharge to a degree of saturated water absorption of from 1 to 1,000 times the self-weight thereof at room temperature under normal pressure. In order that the polymer may absorb such fluid, the polymer chain must have a functional group having a high affinity for such fluid. The functional group includes, for example, (partially) neutralized carboxylic acid, carboxylic acid, (partially) neutralized sulfonic acid, sulfonic acid, and hydroxyl group. Of those, preferred is partially-neutralized carboxylic acid. For the monomer capable of giving a partially-neutralized carboxylic acid to the polymer chain, preferred is unsaturated carboxylic acid; and more preferred is acrylic acid.

The polymer may have a linear molecular structure, but must sustain its shape even after it has absorbed a desired fluid and has swollen. Accordingly, in general, the polymer is preferably crosslinked to have a crosslinked polymer chain structure in order that the polymer chain does not dissolve. The crosslinking may be in any mode of chemical crosslinking such as covalent bonding or ionic bonding or physical crosslinking such as polymer chain entanglement. In view of the chemical stability thereof, chemical crosslinking is preferred, and covalent bonding is more preferred.

Accordingly, the water-absorbent polymer is preferably a crosslinked polymer of unsaturated carboxylic acid, and more preferred is a crosslinked polymer of acrylic acid.

(Shape)

The water-absorbent polymer in the composite A is a nearly spherical particle. "Nearly spherical" as referred to herein is meant to indicate a shape that is true spherical or oval as a whole, and it may have microscopic roughness such as creases, projections and depressions in its surface. It may also have voids such as holes or cracks in its surface or inside it. Preferably, the particle size of the water-absorbent polymer particles is 50 to 1,000 micrometers. More preferably, the particle size thereof is 100 to 900 micrometers, even more preferably 200 to 800 micrometers.

Irregular shape of particles having sharply cut edges like ordinary ground water-absorbent polymer particles are defective in that they irritate skin and their sharply cut edges are broken to give fine particles when having received mechanical load applied thereto. The nearly spherical, water-absorbent polymer particles as in the invention are free from the drawbacks of such irregular shape of particles. As compared with irregular shape of particles, in addition, another advantage of the nearly spherical, water-absorbent polymer particles is that they accept closest packing and therefore can form high-density composites.

2) Bonding Fibers

As so mentioned hereinabove, the bonding fibers include partially-wrapped fibers and surface-adhering fibers. These fibers are described in detail hereinunder.

(Type of Fibers)

The fibers may be any of synthetic fibers, natural fibers, semi-synthetic fibers, or inorganic fibers. Preferably, the fibers firmly adhere to the water-absorbent polymer both before water absorption and after water absorption for better fixation of the water-absorbent polymer.

It is known that different substances having a high affinity for each other firmly adhere to each other, in general. Water-absorbent polymer is one of substances that are the most hydrophilic. To that effect, it may be said that fibers having a larger degree of hydrophilicity may have a larger degree of adhesiveness. The contact angle of a water drop on fibers may be considered as the quantitative criterion for the degree of hydrophilicity of the fibers. Concretely, when the contact angle of a water drop on fibers is smaller (or that is, when the fibers are more hydrophilic), then the adhesiveness of the fibers may be larger; but on the contrary, when the contact angle is larger (that is, when the fibers are less hydrophilic), then the adhesiveness of the fibers tend to be smaller. To that effect, the contact angle of a water drop on the surface of the fiber material is preferably at 60° or less, more preferably at 50° or less most preferably at 40° or less. Hydrophilic fibers having such a large degree of hydrophilicity include cellulosic fibers of pulp, rayon, cotton, regenerated cellulose, as well as polyamide fibers, polyvinyl alcohol fibers and the like. When such hydrophilic fibers are used, then their adhesiveness to water-absorbent polymers may be enhanced and, in addition, other functions of the hydrophilic fibers, for example, their function of conducting water to water-absorbent polymers (water conductivity) may also be enhanced. Especially for sanitary materials, pulp fibers are preferred to other hydrophilic fibers as they do not irritate skins and they have a soft feel.

On the other hand, hydrophobic fibers may be combined with fibers showing little hydrophilic property, i.e. hydrophilic fibers, from the viewpoint of the water permeability and the water dispersibility through the composite. Examples of hydrophobic fibers usable herein include polyester fibers, polyethylene fibers, polypropylene fibers, polystyrene fibers, polyvinyl chloride fibers, polyvinylidene chloride fibers, polyacrylonitrile fibers, polyurea fibers, polyurethane fibers, polyfluoroethylene fibers, and polyvinylidene cyanide fibers. In one embodiment of the invention, hydrophilic fibers are selected for partially-wrapped fibers and hydrophobic fibers are selected for surface-adhering fibers. In this embodiment, the hydrophobic fibers therein are expected to improve the water diffusion in the water-absorbent polymer particles.

The hydrophilicity and the hydrophobicity of the series of fibers exemplified herein are not absolute ones, and they may vary depending on the starting monomers and on the presence or absence of modification of the fibers. Accordingly, the hydrophilicity and the hydrophobicity of the fibers to be used herein shall be evaluated through determination of the contact angle on them. The contact angle depends on the shape of the fiber material to be used in the test and the surface smoothness thereof. In the invention, the contact angle is the contact angle of a drop of distilled water to a smooth surface of a film or sheet formed by fiber material, measured by the use of the device mentioned below.

(Shape)

From the viewpoint of gel blocking prevention, it is a matter of importance to select the fibers in consideration of the stiffness of the fibers and the fiber diameter that are mentioned hereinunder.

Preferably, the bonding fibers for use in the invention have an average fiber length of 50 to 50,000 micrometers as stated above. More preferably, it is 100 to 30,000 micrometers, further more preferably 500 to 10,000 micrometers. Fibers having an excessively-long fiber length will adhere to multiple water-absorbent polymer particles and therefore could not ensure the independency of the individual water-absorbent polymer composites, and if so, a composition comprising the polymer composites will be difficult to be opened. Contrary to this, fibers having an extremely-short fiber length will be difficult to be wrapped in or adhere to the water-absorbent polymer particles.

For obtaining the preferable shape of the composition A, the ratio of particle size of the water-absorbent polymer/fiber length is preferably 2:1 to 1:1,000, more preferably 1:1 to 1:500, even more preferably 1:2 to 1:100.

Also preferably, the binding fibers for use in the invention have a fiber diameter of 0.1 to 500 decitex, more preferably 0.1 to 100 decitex, even more preferably 1 to 50 decitex, still more preferably 1 to 10 decitex. Fibers having an extremely-large diameter will be too stiff to be wrapped in or adhered to the water-absorbent polymer particles, and, in addition, they may be difficult to be molded under compression and will be therefore unfavorable for thinned articles. For use in sanitary goods and others, such thick fibers are unfavorable since they are hard to the touch and will irritate the users' skins and they have a rough feel. Contrary to this, fibers having an extremely-small diameter may also be unfavorable since such thin fibers could not ensure the water transferability and diffusibility. In addition, they are not stiff, and will inevitably form clumps of the water-absorbent polymer.

The appearance of the fiber may be straight or curly. For example, the fiber may curl without tension.

Taking the matters mentioned above into consideration, the type, the length, the diameter and appearance of the fibers for use herein shall be suitably selected and determined.

(Partially-wrapped Fibers)

The partially-wrapped fibers fill the role of ensuring the fixation of the water-absorbent polymer. The fibers improve the water-absorbent polymer fixation before and after water absorption. Specifically, the fibers extending from the surface of the water-absorbent polymer prevent the rotary motion and the translation motion of the water-absorbent polymer while under pressure. A part of the fibers are wrapped in the water-absorbent polymer and, even after water absorption, they do not remove from the water-absorbent polymer. Accordingly, the fibers exhibit an important role in polymer fixation after water absorption. Regarding the shape of the fibers for use herein, they may be hollow fibers or side-by-side fibers with improved water transferability.

When the partially-wrapped fibers consist of hydrophilic fibers, the fibers act to improve the water transferability into the water-absorbent polymer. Accordingly, water can be directly led into the water-absorbent polymer via the fibers. For more effectively exhibiting this function, it is desirable to select and use fibers of high water transferability that will be described hereinunder.

Further, the fibers play a role of ensuring the independency of the individual water-absorbent polymer composites. In the process of polymerizing the composite precursor, the fibers act to prevent the water-absorbent polymer particles from fusing to each other owing to their mutual steric hindrance. Specifically, the fibers that extend from the water-absorbent polymer surface keep the polymer particles being formed through polymerization, at a distance to thereby prevent them contacting and from fusing together. As a result, each water-absorbent polymer composite (precursor) keeps its independency, not adhering to the reactor wall in the production step and in the treatment step, and therefore ensures opening property of the composition that will be mentioned hereinunder.

On the other hand, the fibers give suitable physical entanglement to the individual water-absorbent composites, and when a plurality of the composites are thus gathered into masses, the fibers therein further give shape retentivity to the composite masses. The shape retentivity means that the composite masses are not readily broken into pieces by their self-weight or so. Specifically, the composite A have shape retentiveness by themselves even when any free fibers or the like are not added thereto. Accordingly, when a composition is formed from the composite A, the composition has an especially characteristic feature of opening property and shape-sustainability. Moreover, the fibers impart a soft and smooth feeling to the composite A. Since the water-absorbent polymer particles are nearly spherical in addition to the function of the fibers, the composite A gives extremely soft feeling when pressed even in dry and is therefore favorable for sanitary materials, etc.

(Surface-adhering Fibers)

The surface-adhering fibers are effective for ensuring the fixation of the water-absorbent polymer before water absorption. Further, after the water-absorbent polymer particles have been swollen, the fibers on the surfaces of the polymer particles form a space between the neighboring polymer particles to ensure the water flow route therebetween. For attaining this effect, it is not always necessary that the fibers still adhere to the water-absorbent polymer particles even after water absorption, but it is desirable that at least the fibers are densely arranged on the surface of the water-absorbent polymer. For this, it is convenient that the fibers adhere to the surface of the water-absorbent polymer before water absorption, as in the invention. As the case may be, it will be also favorable to use fibers that are stiff in some degree for forming a space between the neighboring water-absorbent polymer particles to ensure the water flow route therebetween. Combined with the effect of the above-mentioned partially-wrapped fibers that are wrapped in the water-absorbent polymer, it will be also effective for ensuring the fixation of the water-absorbent polymer before water absorption. Regarding the shape of the fibers for use herein, they may be hollow fibers or side-by-side fibers with improved diffusibility.

When the surface-adhering fibers consist of hydrophilic fibers, the fibers are effective for preventing the gel blocking (lumps-forming) phenomenon. The blocking phenomenon means that the polymer having absorbed water is swollen and forms lumps through contact of the swollen polymer particles to interfere with the water flow through the polymer composite. When the composite has absorbed water, the hydrophilic fibers fill the role of uniformly transferring and diffusing water to the surface of every water-absorbent polymer particle. When the surface-adhering fibers consist of hydrophobic fibers, the fibers exhibit the function of improving the water diffusion in the water-absorbent polymer particles.

Further, the fibers have similar functions and exhibit similar effects to the partially-wrapped fibers described above. The surface-adhering fibers ensure the independence of the individual polymer composites, shape-sustainability and a soft and smooth feeling.

3. Characteristics

1) Compatibility of Fixation with Water-absorbing Capacity (Composite Effect of Fibers)

In general, the fixation security of the water-absorbent polymer is inconsistent with the retentiveness of the water-absorbing capacity such as water retentiveness and the security of the water-absorbing capacity under pressure thereof. Accordingly, when the water-absorbent polymer particles are intended to ensure still good fixability not only before water absorption but also after water absorption, they require strong adhesiveness of the water-absorbent polymer and the fibers even after water absorption far over their water-absorbing expansion power. This means that the fibers cause water-absorbing swelling retardation of the water-absorbent polymer, not giving any good water-absorbing capacity. Contrary to this, if the adhering surface of the water-absorbing polymer and the fibers is made to be freely swellable for ensuring the water-absorbing capacity such as water retentiveness and water-absorbing capacity under pressure of the polymer, the adhering surface between the water-absorbent polymer and the fibers will be broken and the polymer will lose satisfactory fixability.

In the composite A of the invention, both the partially-wrapped fibers and the surface-adhering fibers are indispensable. Specifically, if the composite contains only the former fibers, it is not effective for preventing the gel blocking (lumps-forming) phenomenon in water absorption. On the other hand, if it contains only the latter fibers, the fixation of the water-absorbent polymer therein after water absorption is unsatisfactory. Accordingly, for exhibiting the above-mentioned effect anytime before and after water absorption, the fibers of the two types are both indispensable. The coexistence of the fibers of the two types has made it possible to attain both the fixation security and the water-absorption security of the water-absorbent polymer, which are heretofore inconsistent to each other. Specifically, the remarkable feature of the composite A is that the composite ensures good fixation not only before water absorption but also after water absorption, and further ensures not only retentiveness but also water-absorbing capacity under pressure. The material of the two types of the fibers may be the same or different, and may be suitably selected in accordance with the use and the object of the polymer composite and for exhibiting the respective effects of the fibers.

2) Opening Property

One characteristic feature of the composite A is that mass of the composite A can be opened and a water-absorbent polymer composite composition comprising the composite A can be opened. This feature can be obtained by the fact that the individual composites are substantially independent of each other. Specifically, it is desirable that the fibers of constituting one composite do not substantially adhere to any other composite. For this, it is desirable that the length of the fibers to be used is suitably selected although it varies depending on the production condition. The opening property may be evaluated on the basis of the easiness in worsted spinning and on the broken condition of the water-absorbent polymer particles after worsted spinning, for example, as mentioned hereinunder.

3) Shape Sustainability

The composite A is characterized in that not only its masses have shape sustainability but also it gives shape sustainability to the absorbent polymer composite composition that contains the composite A. As so mentioned hereinabove, the bonding fibers in the composite A give suitable physical entanglement to the individual water-absorbent composites, and when the composite A-containing water-absorbent polymer composite composition is formed into masses, then the fibers therein give shape sustainability to the composition masses. The shape sustainability means that the composition masses are not readily broken into pieces by their self-weight or so.

II. Composition of the Invention

1. Structure:

The composition of the invention is characterized in that it comprises the above-mentioned composite A, and it may contain any other constitutive components, for example, the following composite B and composite C, and free fibers. In the composition of the invention, the dry weight ratio of all fibers (bonding fibers+free fibers) to the water-absorbent polymer particles is generally in the range of 70:30 to 2:98, but preferably 50:50 to 5:95, more preferably 30:70 to 5:95. The ratio of the bonding fibers to all fibers is generally in the range of 3 to 100%.

Preferably, the composition of the invention has a bulk density of 0.15 to 0.85 g/cm$^3$, more preferably 0.20 to 0.85 g/cm$^3$, even more preferably 0.30 to 0.85 g/cm$^3$. The constitutive components of the composition of the invention are independent of each other and are openable, and the composition is therefore openable by itself.

2. Constitutive Components

1) Composite A

The composition of the invention contains the composite A generally in a weight fraction of 1 or less, but preferably at least 0.1, more preferably at least 0.2, even more preferably at least 0.3. Preferably, the average particle size of the water-absorbent polymer particles that constitute the composite A to be in the composition of the invention is 50 to 1,000 micrometers, more preferably 100 to 900 micrometers, even more preferably 200 to 800 micrometers. Also preferably, the average fiber length of the fibers that constitute the composite A to be in the composition of the invention is 50 to 50,000 micrometers, more preferably 100 to 30,000 micrometers, even more preferably 500 to 10,000 micrometers. Also preferably, the average fiber diameter of the fibers that constitute the composite A to be in the composition of the invention is 0.1 to 500 decitex, more preferably 0.1 to 100 decitex, even more preferably 1 to 50 decitex, still more preferably 1 to 10 decitex.

2) Composite B

The "composite B" is a "water-absorbent polymer composite that comprises one or more water-absorbent polymer particles and one or more fibers, in which the water-absorbent polymer particles are nearly spherical, and each fiber is partially wrapped in the polymer particle and partially exposed outside it, but does not adhere to the surface of the polymer particle". One or more bonding fibers that bond to the water-absorbent polymer in the composite B are partially-wrapped fibers, and do not include surface-adhering fibers. Accordingly, the indispensable constitutive elements of the composite B are the following two, and surface-adhering fibers are not the constitutive element of the composite B.

<1> Water-absorbent polymer particles,
<2> Partially-wrapped fibers.

The fibers in the composite B may be selected, like those mentioned hereinabove in the section of bonding fibers for the composite A. The weight fraction of the composite B in the composition of the invention is generally 0 to 90% by weight. If the composite B is too much, then it will detract from water-absorbent polymer fixation before water absorption.

3) Composite C

The "composite C" is a "water-absorbent polymer composite that comprises one or more water-absorbent polymer particles and one or more fibers, in which the water-absorbent polymer particles are nearly spherical, and each fiber partially adheres to the surface of the polymer particle but is not wrapped in the polymer particle". One or more bonding fibers that bond to the water-absorbent polymer in the composite C are surface-adhering fibers, and do not include partially-wrapped fibers. Accordingly, the indispensable constitutive elements of the composite C are the following two, and partially-wrapped fibers are not the constitutive element of the composite C.

<1> Water-absorbent polymer particles,
<2> Surface-adhering fibers.

The fibers in the composite C may be selected, like those mentioned hereinabove in the section of bonding fibers for the composite A. The weight fraction of the composite C in the composition of the invention is generally 0 to 90% by weight. If the composite C is too much, then it will detract from gel fixation after water absorption.

The weight ratio of composites A to C may be generally A:B:C=(10 to 100):(0 to 90):(0 to 90).

4) Free Fibers:

"Free fibers" are "fibers neither wrapped in nor adhering to water-absorbent polymer particles". The composition of the invention may contain one or more such free fibers. The free fibers in the composition improve the flexibility, the soft touch, the water conductivity, the water permeability, the water diffusibility and the vapor permeability.

Like the bonding fibers mentioned above, the free fibers may also be any of synthetic fibers, natural fibers, semi-synthetic fibers, inorganic fibers, etc. The fibers to be used shall be selected in accordance with the use and the object of the water-absorbent polymer composite composition to be provided herein. For example, when the composition is used for water-absorbent articles, preferably selected for these are hydrophilic fibers. The hydrophilic fibers include cellulosic fibers of pulp, rayon, cotton, regenerated cellulose, as well as polyamide fibers and polyvinyl alcohol fibers. When such hydrophilic fibers are used, then the water conductivity of the composition may be increased. Especially for sanitary materials, pulp fibers are preferred to other hydrophilic fibers as they do not irritate skins and they have a soft feel.

On the other hand, hydrophobic fibers may be used for the free fibers. For example, usable are polyester fibers, polyethylene fibers, polypropylene fibers, polystyrene fibers, polyvinyl chloride fibers, polyvinylidene chloride fibers, polyacrylonitrile fibers, polyurea fibers, polyurethane fibers, polyfluoroethylene fibers, polyvinylidene cyanide fibers. Using these hydrophobic fibers may improve the water permeability and the water diffusibility of the composition.

Different from the bonding fibers mentioned above, the free fibers are not specifically defined in point of their affinity for the water-absorbent polymer for use herein and for the water-absorbent polymer composite of the invention.

The type of the fibers that are usable for the free fibers may be the same as or different from that of the bonding fibers to be in the composite A, the composite B or the composite C. For example, hydrophilic fibers may be selected for the bonding fibers, and hydrophobic fibers may be selected for the free fibers. In this embodiment, if employed, the hydrophobic fibers exhibit the function of improving the water dispersibility through the water-absorbent polymer composite segments. From the viewpoint of blocking prevention, it is also important to specifically select the fibers in consideration of the stiffness and the diameter of the fibers that will be mentioned hereinunder.

The free fibers used in the composition of the invention preferably have a fiber length of 50 to 100,000 μm. More preferably, their fiber length is 100 to 5,000 μm, even more preferably 500 to 2,000 μm. If the fiber length is extremely long, the composition will be difficult to open. On the contrary, if the fiber length is extremely short, the fibers themselves will be very movable and will be therefore problematic in that they will release from the composition.

The free fibers used in the composition of the invention preferably have a fiber diameter of 0.1 to 5,000 dtex, more preferably 0.1 to 100 dtex, even more preferably 1 to 50 dtex, still more preferably 1 to 10 dtex. If the fiber diameter is extremely large, the fibers will be too stiff and will be therefore difficult to mix with the water-absorbent polymer composite. If so, in addition, they are unsuitable to compression molding and will be therefore unfavorable to thin articles. Moreover, when used in sanitary goods and the like, they will be hard and will irritate skins, and their feeling will be not good. On the contrary, if the fiber diameter is extremely small, the fibers will be too thin and therefore could not ensure the above-mentioned water permeability and dispersibility. If so, in addition, the fibers are not stiff and will form lumps.

The dry weight ratio of the free fibers to the water-absorbent polymer may be generally in the range of 95:5 to 0:100, more preferably 95:5 to 5:95. If the ratio of the free fibers is too high, then it is unfavorable since the water-absorbent polymer could not substantially exhibit its effect and since the bulk density of the composite composition will reduce. In general, the free fibers account for 90% or less by weight of the composition of the invention.

III. Method for Production

IIIA. Method for Production of Composite A

1. Starting materials

1) Monomers (Types)

Polymerizable monomer used for producing the water-absorbent polymer particles in composite A is not specifically defined in point of its type, so far as it gives a water-absorbent polymer. Especially preferred for use herein are polymerizable monomers of which the polymerization is initiated by a redox initiator. The monomers for use herein may generally be preferred to be water-soluble.

Typical and preferred examples of the monomer for use in the invention are aliphatic unsaturated carboxylic acids and their salts. Concretely, they include unsaturated monocarboxylic acids and their salts such as acrylic acid and its salts, methacrylic acid and its salts; and unsaturated dicarboxylic acids and their salts such as maleic acid and its salts, itaconic acid and its salts. One or more of these may be used herein either singly or as combined. Of those, more preferred are acrylic acid and its salts, and methacrylic acid and its salts; and even more preferred are acrylic acid and its salts.

As mentioned hereinabove, the polymerizable monomer to give the water-absorbent polymer for use in the invention is preferably an aliphatic unsaturated carboxylic acid or its salts. Therefore, for the aqueous solution of the polymerizable monomer, preferred is an aqueous solution that comprises any of an aliphatic unsaturated carboxylic acid or its salts as a main ingredient. The aqueous solution "that comprises any of an aliphatic unsaturated carboxylic acid or its salts as a main ingredient" is meant to indicate that the content of the aliphatic unsaturated carboxylic acid or its salt in the solution is at least 50 mol %, preferably at least 80 mol % of the total amount of the polymerizable monomers therein.

The salts of aliphatic unsaturated carboxylic acid are generally water-soluble salts, including, for example, alkali metal salts, alkaline earth metal salts and ammonium salts. The degree of neutralization of the salts may be suitably determined in accordance with the object thereof. For salts of acrylic acid, it is desirable that 20 to 90 mol % of the carboxyl group therein is neutralized to be an alkali metal salt or an ammonium salt. If the degree of partial neutralization of the acrylic acid monomer is extremely small, the water absorbancy of the water-absorbent polymer formed from the monomer may be significantly lower.

For neutralizing acrylic acid monomers, alkali metal hydroxides and bicarbonates, ammonium hydroxide, and other materials can be used. Preferred are alkali metal hydroxides such as sodium hydroxide and potassium hydroxide.

In the invention, the above-mentioned aliphatic unsaturated carboxylic acids may be copolymerized with any other polymerizable monomers that are copolymerizable with them. Examples of such polymerizable monomers include (meth)acrylamide, (poly)ethylene glycol (meth)acrylate and 2-hydroxyethyl (meth)acrylate. Alkyl acrylates such as methyl acrylate or ethyl acrylate can also be used as the polymerizable monomers although they are poorly water-soluble monomers. These polymerizable monomers can be used within the range not detracting from the properties of the water-absorbent polymers formed. In this description, the terminology "(meth)acryl" is meant to indicate both "acryl" and "methacryl".

Of the polymerizable monomers, those that give water-absorbent polymers may also be used as main monomers in the "aqueous solution of a polymerizable monomer of giving a water-absorbent polymer" not as the auxiliary components for the aliphatic unsaturated carboxylic acid or its salts.

(Concentration of the Monomer)

In the aqueous solution of a polymerizable monomer that contains any of the above-mentioned aliphatic unsaturated carboxylic acids or its salts as a main ingredient, the concentration of the polymerizable monomer may be preferably at least 20 wt %, more preferably at least 25 wt %. If the monomer concentration is lower than 20 wt %, the water absorbancy of the water-absorbent polymers obtained after polymerization tends to be unsatisfactory. The uppermost limit of the polymer concentration may be 80 wt % or so in view of the handlability of the polymerization liquid.

2) Crosslinking Agent

The aliphatic unsaturated carboxylic acid or its salts, especially acrylic acid or its salts may form self-crosslinked polymers by themselves, but may be combined with a crosslinking agent to positively form a crosslinked structure. When a crosslinking agent is used for polymerizing the monomers, the water absorbency of the water-absorbent polymers formed generally increases. For the crosslinking agent, preferably used are polyvinyl compounds that are copolymerizable with the above-mentioned polymerizable monomers, for example, N,N'-methylenebis(meth)acrylamide and (poly)ethylene glycol poly(meth)acrylates, as well as water-soluble compounds having at least two functional groups capable of reacting with carboxylic acids, for example, polyglycidyl ethers such as ethylene glycol diglycidyl ether and polyethylene glycol diglycidyl ether. Of those, especially preferred is N,N'-methylenebis(meth)acrylamide. The amount of the crosslinking agent to be used may be 0.001 to 1 wt %, but preferably 0.01 to 0.5 wt % of the amount of the monomer fed for polymerization.

3) Polymerization Initiator

The polymerization initiator for use in the invention may be any one usable in radical polymerization in aqueous solution. Such the initiator includes inorganic and organic peroxides, such as ammonium persulfates, alkali metal especially potassium persulfates, hydrogen peroxide, t-butyl peroxide, acetyl peroxide, etc.

Also usable are other known azo initiators. For example, usable is 2,2'-azobis(2-amidinopropane) dihydrochloride that is soluble in water in some degree.

The polymerization is initiated through decomposition of the radical polymerization initiator. Pyrolysis is one well-known process. A polymerization initiator not heated may be added to a monomer reaction solution that has been previously heated up to the decomposition point of the polymerization initiator to thereby initiate the polymerization. This case is also within the technical scope of pyrolysis.

The initiator preferably used in the invention is a redox system that is soluble in water in some degree, or that is, a combination of an oxidizing agent and a reducing agent.

The oxidizing agent includes, for example, hydrogen peroxide, persulfates such as ammonium persulfate, potassium persulfate; as well as t-butyl hydroperoxide, cumene hydroperoxide, ceric salts, permanganates, chlorites, hypochlorites, etc. Of those, especially preferred is hydrogen peroxide. The amount of the oxidizing agent to be used may be 0.01 to 10 wt %, but preferably 0.1 to 2 wt % of the polymerizable monomer.

4) Fibers

Type and shape of the fibers can be determined based on the above description.

Regarding their microscopic condition, it is desirable that the fibers are dispersed as uniformly as possible. In general, fibers are often entangled to form fiber masses. In the invention, the apparent fiber mass diameter is preferably at most 20 mm, more preferably at most 10 mm, most preferably at most 5 mm. Needless-to-say, it is desirable that the fibers are independently separated from each other. For ensuring the uniformity of the fibers, generally employed is a method of opening the fibers. "Opening" as referred to herein includes both concepts of refining and fibrillation. Refining includes tearing and pulverizing nylon and the like sheets into strips and fibers, etc. Fibrillation includes tearing and beating cellulose paper into pulp, etc.

Concretely, it is described in *Fiber Handbook (for processing fibers)* (edited by the Society of Fiber Technology of Japan, published by Maruzen, 1969), page 18, ff. For it, for example, usable is any of cotton-spinning type, worsted-spinning type, woollen-spinning type, hard and bast fiber-spinning type, waste silk-spinning type or rotor blade type grinding machines, hammer type grinding machines, pulp fibrillating machines and others introduced in that document. Also employable for it is a technique of flocking, which comprises electrically charging fibers to thereby make them all substantially independent of each other for uniform dispersion thereof; based on the electrostatic repulsion of the fibers.

2. Process for Production

1) Polymerization Step

The method for producing the water-absorbent polymer composite of the invention is not specifically defined so far as it gives the water-absorbent polymer composite that satisfies the requirements claimed herein.

One preferred embodiment of producing it comprises adding a redox-type polymerization initiator to an aqueous solution of a polymerizable monomer that gives a water-absorbent polymer, for example, to an aqueous solution of a polymerizable monomer that comprises as a main ingredient, an aliphatic unsaturated carboxylic acid or its salt to thereby initiate the polymerization of the monomer, forming the reaction mixture that is under polymerization and contains the monomer after the start of the polymerization and the polymer formed, into droplets in a gas phase, contacting the resulting droplets with fibers that have been fed into the gas phase and have been dispersed therein, to thereby form a water-absorbent polymer composite precursor, finally completing the polymerization in the precursor to give the intended, water-absorbent polymer composite, and collecting it. One preferred method of polymerizing the droplets in a gas phase comprises mixing a first liquid of an aqueous solution of a polymerizable monomer that contains any one of the oxidizing agent and the reducing agent to constitute the redox-type polymerization initiator, with a second liquid of an aqueous solution that contains the other agent of the redox-type polymerization initiator and optionally the polymerizable monomer, in a gas phase so as to initiate the polymerization of the monomer.

Concretely, for example, the first liquid and the second liquid are impinged through different nozzles in such a manner that the two liquid jets may colloid with each other at a crossing angle of at least 15 degrees to form a liquid column. Thus colliding with each other at such a crossing angle, the liquid jets utilize a part of the energy of the jets from the nozzles for mixing them. The angle at which the jets of the first and second liquids from the respective nozzles cross each other shall be suitably determined depending on the property of the polymerizable monomer used and the flow rate of the liquid jets. For example, when the linear speed of the liquid jets is large, then the crossing angle may be small.

In this case, the temperature of the first liquid may be generally from room temperature to about 60° C., preferably from room temperature to about 40° C.; and that of the second temperature may also be generally from room temperature to about 60° C., preferably from room temperature to about 40° C.

In the manner as above, the aqueous solutions having been impinged through the respective nozzles are made to collide with each other while they still form separate liquid columns, and are thus mixed together. After thus mixed, they form a liquid column and keep it for a while. Then, the liquid column is broken into droplets. In the thus-formed falling droplets, the polymerization of the monomer further goes on in a gas phase.

In order that the droplets are contacted with fibers during the polymerization to form a suitable water-absorbent polymer composite, the size of the droplets is preferably 50 to 1,000 micrometers. Also preferably, the space density of the droplets in the reactor is in the range of 0.1 to 10,000 $g/m^3$. If it oversteps the uppermost limit, some water-absorbent polymer could not be contacted with fibers; but if it is lower than the lowermost limit, some fibers could not be contacted with the water-absorbent polymer. Anyhow, if so, the yield of the water-absorbent polymer composite may be relatively lower.

The gas to give the gas phase for the reaction site in which the polymerization starts to form the droplets still under polymerization is preferably inert to polymerization, and is, for example, nitrogen, helium or carbon dioxide. The gas may also be air. The humidity in the gas is not specifically defined, including water vapor alone. However, if the humidity is too low, the water will vaporize from the aqueous monomer solution before the monomer polymerization goes on, and, as a result, the polymerization speed will be extremely lowered or the polymerization may stop on its way. The temperature of the gas may be from room temperature to 150° C., preferably up to 100° C. The gas flow direction may be any of counter flow or parallel flow relative to the direction in which the liquid column and the droplets run. However, when the time for which the droplets stay in the gas phase must be prolonged, or that is, when the degree of polymerization of the polymerizable monomer must be increased so as to increase the viscosity of the droplets, the gas flow is preferably a counter flow (in the direction opposite to the gravity).

2) Step of Fiber Feeding

When the droplets are contacted with fibers, the monomer conversion in the droplets (hereinafter referred to as "degree of polymerization") is preferably in the range of 0 to 90%, more preferably 0 to 80%, most preferably 0 to 70%. If the degree of polymerization is higher than 90%, there will be a probability that the fibers could be neither wrapped in nor adhered to the water-absorbent polymer.

For obtaining the structure of the composite A, fibers may normally be applied to the polymer in one and the same reaction stage where the degree of polymerization is nearly the same, but may preferably be applied to the polymer in at least two reaction stages that differ in the degree of polymerization therein. For this, it is desirable that the fibers are fed into the system through multiple supply ports. Specifically, when the fibers are partially wrapped in the water-absorbent polymer, it is desirable that they are contacted with the droplets in a stage in which the degree of polymerization is relatively low, but when the fibers are surface-adhering fibers, it is desirable that they are contacted with the droplets in a stage in which the degree of polymerization is relatively high.

For forming both the partially-wrapped fibers and the surface-adhering fibers, it is desirable that the polymerization degree difference between the two in the contact site where the fibers are contacted with the monomer is in the range of 10% to 80%, more preferably 10 to 70%, most preferably 10 to 60%. The degree of polymerization in each contact site shall be suitably determined depending on the type of the monomer and the type of the fibers.

For obtaining a larger amount of the structure of the composite B, it is desirable that the fibers are fed into the system in a stage in which the degree of polymerization is relatively low (for example, in the range of 0 to 60%); and for obtaining a larger amount of the structure of the composite C, it is desirable that the fibers are fed into the system in a stage in which the degree of polymerization is relatively high (for example, in the range of 30 to 90%).

3) Step of Fiber Transfer

For feeding the fibers into the reaction field so as to make them contacted with the droplets under polymerization, any known transfer method is employable. The space density of the fibers in the reactor is preferably in the range of 0.005 to 1,000 $g/m^3$, more preferably 0.5 to 1,000 $g/m^3$, when the fibers are partially wrapped in the water-absorbent polymer. If the space density is too large, then some fibers could not be wrapped in the water-absorbent polymer; but if it is too low, then some water-absorbent polymer will be useless, not serving for wrapping the fibers therein. Anyhow, if so, it is problematic in that the yield of the water-absorbent polymer composite relatively lowers. For efficient contact between the fibers and the droplets, it is desirable that the ratio of the space density of the fibers to the space density of the droplets is in the range of 0.01 to 100, more preferably 0.05 to 50, even more preferably 0.1 to 10. If the ratio of the space density of the fibers to that of the droplets is too small, then the fibers are not almost contacted with the droplets; but if too large, then too many free fibers may be formed and they may lower the production efficiency. For feeding the fibers as fine and uniformly as possible to the system, it is desirable that the fibers are fed thereinto as a mixed phase flow with a gas. The gas for the mixed phase may be the same as that mentioned hereinabove for the gas of the gas phase to give the above-mentioned reaction site. Above all, air is preferred from the economical viewpoint and from the viewpoint of reducing the environmental load.

Preferably, the weight ratio of the fibers to the air is 1 or less; and that of the linear velocity of the gas is in the range of 1 to 50 m/sec. If the flow rate oversteps the upper limit, it will disturb the trace of the reaction mixture under polymerization in the reaction field, and will be problematic in that some deposit adheres to the inner wall of the reactor. On the other hand, if it is lower than the defined range, the fiber uniformity may not be ensured.

The temperature of the gas to form the mixed phase flow is preferably determined in the range not significantly interfering with the monomer polymerization. To that effect, concretely, the temperature may fall within the range of from room temperature to 150° C., preferably up to 100° C. From the viewpoint of good fiber transferability, the humidity in the gas is as low as possible, but if it is too low, the humidity in the reactor may be thereby lowered and the water will vaporize from the aqueous monomer solution to deposit the monomer before the monomer polymerization goes on, and, as a result, the polymerization speed will be extremely lowered or the polymerization may stop on its way.

4) Other Additional Steps

Some additional steps may be added to the method of producing the water-absorbent polymer composite of the invention. For example, they are a step of processing the remaining monomer; a surface-crosslinking step; and a step of adding some additives to the composite for imparting various additional functions thereto. Examples of the additives include catalysts, reducing agents, deodorizers, human urine stabilizers, antimicrobial agents, etc.

(Method for Processing the Remaining Monomer)

For processing the remaining monomer, for example, employable are (1) a method of further polymerizing the monomer, (2), a method of converting the monomer into some other derivative, and (3) a method of removing the monomer.

The method (1) of further polymerizing the monomer includes a method of further heating the composite of the water-absorbent polymer and the fibers; a method of adding a catalyst or a catalyst component capable of promoting the monomer polymerization to the water-absorbent polymer composite followed by heating it; a method of exposing the polymer composite to UV rays; and a method of exposing it to electromagnetic radiations or to particulate ionizing radiations.

The method of further heating the water-absorbent polymer composite comprises heating the composite at 100 to 250° C. to thereby polymerize the monomer that remains in the composite.

Regarding the method of adding a catalyst or a catalyst component capable of promoting the monomer polymerization to the water-absorbent polymer composite, a solution of a reducing agent may be added to the water-absorbent polymer composite since the radical generator may often remain in the composite when the monomer polymerization to give the composite is effected in the presence of a redox-type polymerization initiator. The reducing agent may be any of sodium sulfite, sodium hydrogensulfite, L-ascorbic acid or the like that is generally in the redox-type polymerization initiator. In general, the reducing agent in the form of an aqueous 0.5 to 5 wt % solution thereof may be added to the water-absorbent polymer composite. The amount of the reducing agent to be added is preferably in the range of 0.1 to 2 wt % based on the dry polymer weight. The reducing agent solution may be applied to the composite in any desired manner of spraying it on the composite by the use of a sprayer, or dipping the composite in the solution. After having thus received the reducing agent, the water-absorbent polymer composite is then heated so that the polymerizable monomer therein is polymerized. For example, it may be heated up to 100 to 150° C. for 10 to 30 minutes or so. Thus heated, the water content of the water-absorbent polymer composite may lower. However, the water content thereof is still high, the composite may be further dried in a drier to give the intended product, water-absorbent article.

In the method of exposing the water-absorbent polymer composite to UV rays, any ordinary UV lamp may be used, and the irradiation intensity and the irradiation time may vary depending on the type of the fibers used and the amount of the remaining monomer. In general, the composite may be exposed to a UV lamp at an intensity of 10 to 200 W/cm, preferably 30 to 120 W/cm, for an irradiation time of 0.1 seconds to 30 minutes. The lamp-composite distance may be 2 to 30 cm. The water content of the water-absorbent polymer composite in this stage may be generally in the range of 0.01 to 40 parts by weight, but preferably 0.1 to 1.0 part by weight, relative to one part by weight of the dry water-absorbent polymer. If the water content thereof is smaller than 0.01 parts by weight or larger than 40 parts by weight, it is unfavorable since as having a significant influence on the reduction in the remaining monomer. The atmosphere for UV irradiation may be in vacuum or may be in any of inorganic gas such as nitrogen, argon or helium, or in air. The irradiation temperature is not specifically defined, and the object may be satisfactorily attained at room temperature. The UV-irradiating device to be used is not also specifically defined. Herein employable is any desired method, for example, a method of exposing the composite to UV rays while it is kept static for a predetermined period of time; or a method of continuously exposing the composite to UV rays while it is moved on a belt conveyer.

In the method of exposing the water-absorbent polymer composite to radiations, employable are high-energy radiations such as accelerated electron rays or gamma rays. The dose to be given to the composite varies, depending on the remaining monomer content and the water content of the composite. In general, it may be 0.01 to 100 megarads, but preferably 0.1 to 50 megarads. If too much dose over 100 megarads is given to the composite, the water content of the composite will be extremely lowered; but if a dose of smaller than 0.01 megarads is given thereto, composites that are intended in the invention to have increased water absorbancy and increased water-absorbing rate and have significantly reduced monomer residue are difficult to obtain. The water content of the water-absorbent polymer composite to be exposed to radiations in this stage may be generally at most 40 parts by weight, but preferably at most 10 parts by weight relative to 1 part by weight of the polymer in the composite. If the water content of the composite is over 40 parts by weight, it is unfavorable since the water-absorbing rate of the composite is not so much increased and, in addition, too much water in the composite will have a significant influence on the reduction in the non-polymerized monomer therein. The atmosphere in which the composite is exposed to high-energy radiations may be in vacuum or may be in any of inorganic gas such as nitrogen, argon or helium, or in air. Preferably, the atmosphere is in air. When the composite is exposed to high-energy radiations in air, its water absorbancy and water-absorbing rate may be greatly improved and the monomer residue therein may be significantly reduced. The temperature for the irradiation is not specifically defined. The object can be sufficiently attained at room temperature.

The method (2) of converting the monomer into its derivatives includes, for example, a method of adding amine or ammonia to the composite, and a method of adding thereto a reducing agent such as hydrogensulfites, sulfites, or pyrosulfites.

The method (3) of removing the monomer comprises, for example, extraction with an organic solvent or evaporation. In the method of extracting the monomer with an organic solvent, the water-absorbent polymer composite is dipped in a water-containing organic solvent and the remaining monomer is extracted out and removed. For the water-containing organic solvent, usable is any of ethanol, methanol or acetone, and its water content is preferably in the range of 10 to 99 wt %, more preferably 30 to 60 wt %. In general, the solvent having a higher water content can remove the remaining monomer to a higher degree. However, if the water content of the organic solvent used is too high, the energy consumption in the subsequent drying step will increase. The time for which the composite is dipped in the water-containing organic solvent may be generally in the range of 5 to 30 minutes or so. Preferably, some method of promoting the remaining monomer extraction is employed. For example, the composite may be shaken while processed. After dipped in the solvent, the composite is dried in an ordinary drier.

For evaporating the monomer, the composite may be processed with superheated steam or steam-containing gas. For example, saturated steam at 110° C. is further heated up to 120 to 150° C. to be superheated steam, and this is contacted with the composite whereby the monomer residue in the thus-processed composite may be reduced. In this process, it is believed that, while water in the water-absorbent polymer is evaporated as steam, the remaining monomer may be also evaporated and removed from the water-absorbent polymer. According to this process, the remaining monomer may be removed from the composite and, at the same time, the composite may be dried.

(Surface Crosslinking Step)

For further improving the water absorbancy thereof, the water-absorbent polymer may be crosslinked with a crosslinking agent in its surface. A method of applying a crosslinking agent to the surfaces of powdery water-absorbent polymer particles with an appropriate amount of water followed by heating the polymer particles to thereby crosslink the surfaces thereof to improve the properties of the polymer particles is generally known in the art. According to it, it is believed that a crosslinked structure is selectively formed in the surfaces of the polymer particles, and, as a result, when the polymer particles absorb water to swell, they may keep their shape not interfering with their swelling. As in this method, a solution of a surface-crosslinking agent is first applied to the water-absorbent polymer composite. For the surface-crosslinking agent, employable is any of polyfunctional compounds that are copolymerizable with polymerizable monomers, such as N,N'-methylenebis(meth)acrylamide and (poly)ethylene glycol bis(meth)acrylate, or compounds having some functional groups capable of reacting with a carboxylic acid group, such as (poly)ethylene glycol diglycidyl ether. In general, the amount of the surface-crosslinking agent to be used may be 0.1 to 1 wt %, but preferably 0.2 to 0.5 wt % of the water-absorbent polymer composite. Preferably, the surface-crosslinking agent is used as a solution thereof diluted with water, ethanol or methanol to have a concentration of 0.1 to 1 wt %, preferably 0.2 to 0.5 wt %, in order that it may be uniformly applied to the entire surface of the water-absorbent polymer composite. Concretely, it is desirable that the crosslinking agent solution is sprayed by a sprayer or is coated via a roll brush on the water-absorbent polymer composite. If desired, an excess amount of the crosslinking agent solution is applied to the composite, and then the composite is lightly squeezed between squeezing rolls to such a degree that the polymer particles are not crushed, or is blown with air so as to remove the superfluous crosslinking agent solution from it. The crosslinking agent solution may be applied to the composite at room temperature. After given the crosslinking agent solution, the water-absorbent polymer composite is then heated to attain the crosslinking reaction and a crosslinked structure is thereby selectively formed in the surface of the water-absorbent polymer. The condition for the crosslinking reaction may be suitably determined depending on the crosslinking agent used. In general, the composite is reacted with the crosslinking agent applied thereto, at a temperature not lower than 100° C. for at least 10 minutes. In the invention, a crosslinked polymer of an unsaturated carboxylic acid and a crosslinked polymer of a partially-neutralized acrylic acid can be used as preferable water-absorbent polymers.

(Opening of Deposit of Water-absorbent Polymer Composite)

The water-absorbent polymer composite formed is collected as a deposit. The water-absorbent polymer composites are independent of each other and are therefore readily opened. For opening them, the methods mentioned hereinabove in the section of opening fibers are also employable in the same manner. Preferred are devices and conditions not damaging the water-absorbent polymer particles through any mechanical shock applied thereto.

5) Additives

Various additives may be added to the water-absorbent polymer composite or to the water-absorbent polymer composite composition in order that the composite or its composition may have desired functions in accordance with the intended applications thereof. The additives include, for example, stabilizer for preventing polymer decomposition or deterioration owing to the liquid absorbed by the polymer, antimicrobial agent, deodorizer, odor remover, aromatic agent, and foaming agent.

(Stabilizer)

Of those, one example of the stabilizer for preventing polymer decomposition or deterioration owing to the liquid absorbed by the polymer is a stabilizer that prevents the water-absorbent polymer from being decomposed or deteriorated by the discharges (e.g., human urine, feces) or body fluids (e.g., human blood, menstrual discharges, secretions) which the polymer has absorbed. JP-A 63-118375 proposes a method of adding an oxygen-containing reducing inorganic salt and/or an organic antioxidant to polymer; JP-A 63-153060 proposes a method of adding an oxidizing agent to polymer; JP-A 63-127754 proposes a method of adding an antioxidant to polymer; JP-A 63-272349 proposes a method of adding a sulfur-containing reducing agent to polymer; JP-A 63-146964 proposes a method of adding a metal chelating agent to polymer; JP-A 63-15266 proposes a method of adding a radical chain reaction inhibitor to polymer; JP-A 1-275661 proposes a method of adding a phosphinic acid group or phosphinic acid group-containing amine compound or its salt to polymer; JP-A 64-29257 proposes a method of adding a polyvalent metal oxide to polymer; and JP-A 2-255804 and 3-179008 propose a method of producing polymer in the presence of a water-soluble chain transfer agent. These are all applicable to the invention. In addition, the materials and the methods described in JP-A 6-306202, 7-53884, 7-62252, 7-113048, 7-145326, 7-145263, 7-228788 and 7-228790 are all applicable to the invention. Concretely, for example, potassium oxalate titanate, tannic acid, titanium oxide, phosphinic acid amine (or its salts), phosphonic acid amine (or its salts) and metal chelates are usable in the invention. The stabilizers to human urine, human blood and menstrual discharges may be referred to as a human urine stabilizer, a human blood stabilizer, and a menstrual discharge stabilizer, respectively.

(Antimicrobial Agent)

An antimicrobial agent may be used for preventing the composite from being rot by the liquid that the composite has absorbed. For the antimicrobial agent, for example, employable herein are any of those introduced in *Novel Development of Microbicidal and Antimicrobial Technique*, pp. 17-80 (by Toray Research Center (1994)); *Methods of Examination and Evaluation of Antibacterial and Antifungal Agents, and Product Planning*, pp. 128-344 (by NTS (1997)); Japanese Patent 2,760,814; JP-A 39-179114, 56-31425, 57-25813, 59-189854, 59-105448, 60-158861, 61-181532, 63-135501, 63-139556, 63-156540, 64-5546, 64-5547, 1-153748, 1-221242, 2-253847, 3-59075, 3-103254, 3-221141, 4-11948, 4-92664, 4-138165, 4-266947, 5-9344, 5-68694, 5-161671, 5-179053, 5-269164 and 7-165981.

For example, herein usable are alkylpyridinium salts, benzalkonium chloride, chlorhexidine gluconate, pyridione zinc, and silver-containing inorganic powders. Typical examples of quaternary nitrogen-containing antibacterial agents are methylbenzethonium chloride, benzalkonium chloride, dodecyltrimetylammonium bromide, tetradecyltrimethylammonium bromide, and hexadecyltrimethylammonium bromide. Heterocyclic quaternary nitrogen-containing antibacterial agents include dodecylpyridinium chloride, tetradecylpyridnium chloride, cetylpyridinium chloride (CPC), tetradecyl-4-ethylpyridinium chloride, and tetradecyl-4-methylpyridinium chloride.

Other preferred antibacterial agents for use herein are bis-guanides. These are described in detail, for example, in U.S. Pat. Nos. 2,684,924, 2,990,425, 2,830,006 and 2,863,019. 1,6-Bis(4-chlorophenyl)diguanidohexane is the most preferred example of bis-guanides. It is known as chlorhexidine and its water-soluble salts. Especially preferred are chlorhexidine hydrochloride, acetate and gluconate.

Some other types of antibacterial agents are also useful herein. For example, there are mentioned carbanilides, substituted phenols, metal compounds, and rare earth salts of surfactants. The carbanilides include 3,4,4'-trichlorocarbanilide (TCC, trichlorcarban) and 3-(trifluoromethyl-4,4'-dichlorocarbanilide (IRGASAN). One example of the substituted phenols is 5-chloro-2-(2,4-dichlorophenoxy)phenol (IRGASAN DP-300). The metal compounds include graphite and tin salts, for example, zinc chloride, zinc sulfide and tin chloride. The rare earth salts of surfactants are disclosed in EP-A 10819. Examples of the rare earth salts of the type are lanthanum salts of linear C10-18 alkylbenzenesulfonates.

(Deodorizer, Odor Remover and Aromatic Agent)

Deodorizer, odor remover and aromatic agent are used for preventing or reducing the offensive odor of the liquid which the polymer has absorbed. Such deodorizer, odor remover and aromatic agent are introduced in, for example, *Techniques and Views of New Deodorizers and Odor Removers*, (by Toray Research Center (1994)); JP-A 59-105448, 60-158861, 61-181532, 1-153748, 1-221242, 1-265956, 2-41155, 2-253847, 3-103254, 5-269164 and 5-277143, and any of these are usable herein. Concretely, iron complexes, tea extracts and activated charcoal are mentioned for the deodorizer and odor remover. The aromatic agent includes, for example, fragrances (e.g., citral, cinnamic aldehyde, heliotopin, camphor, bornyl acetate), wood vinegar, paradichlorobenzene, surfactants, higher alcohols, and terpene compounds (e.g., limonene, pinene, camphor, borneol, eucalyptol, eugenol).

(Foaming Agent and Foaming Assistant)

A foaming agent or a foaming assistant may be added to the polymer composite for making the composite porous and have an enlarged surface area to thereby further improve the water absorbancy of the water-absorbent polymer in the composite. The foaming agent and the foaming assistant are introduced in, for example, *Chemicals for Rubber and Plastics* (by Rubber Digest, 1989, pp. 259-267), and any of these are usable herein. For example, there are mentioned sodium bicarbonate, nitroso compounds, azo compounds, sulfonyl hydrazide.

These additives may be suitably added to the water-absorbent polymer composite in any stage of producing it, in accordance with the object, the action and the mechanism of the composite. For example, the foaming agent may be added in the step of preparing the water-absorbent polymer, preferably before the start of monomer polymerization or during the polymerization. The human urine stabilizer, the human blood stabilizer, the antimicrobial agent, the deodorizer and the aromatic agent may be added in any step of producing the water-absorbent polymer composite or producing the water-absorbent polymer composite composition or even producing water-absorbent articles of the composite. They may be previously added to fibers.

IIIB. Method for Producing the Composition of the Invention

1. Starting Materials and Production Steps

In general, the composition of the invention may be produced according to a method of mixing and dispersing the composite A that had been previously prepared, with the composite B and/or the composite C and/or free fibers that had been separately prepared (sequential mixing method), or according to a method of producing the composition simultaneously in the polymerization step of giving the composite A (simultaneous mixing method). If desired, the composition may be compressed later.

1) Sequential Mixing Method Later

For example, the deposit composite A or the opened and independent composite A is mixed with the composite B and/or the composite B and/or free fibers in a mixer in any desired ratio to give a water-absorbent polymer composite composition. In this process, a solid mixer may be used that enables power-power mixing, power-fiber mixing or fiber-fiber mixing. Concretely, it is described in detail in *Chemical Engineering II* (by Yoshitoshi Ohyama, Iwanami Zensho, 1963, p. 229). For example, it includes rotary mixers such as cylindrical mixer, V-shaped mixer, double conical mixer, cubic mixer; and fixed mixers such as screw mixer, ribbon mixer, rotary disc mixer, fluidization mixer.

2) Simultaneous Mixing Method

When a reactor is specifically designed in point of the site through which fibers are to be fed into it, then the composition of the invention may be substantially obtained. For example, when droplets are contacted with fibers in a stage in which the degree of polymerization is low, then a composition that contains the composite B may be obtained; but when droplets are contacted with fibers in a stage in which the degree of polymerization is high, then a composition that contains the composite C may be obtained.

On the other hand, when fibers are fed into the system of producing a water-absorbent polymer composite in such a manner that the fibers are not substantially contacted with the water-absorbent polymer under polymerization or with the water-absorbent polymer in the water-absorbent polymer composite composition, then a composition that contain free fibers may be obtained.

3) Compression Method

The composition may be compressed while the pressure thereto and the temperature and the humidity around it are suitably controlled. For example, a tabular press or a roll press may be used. The pressure is not specifically defined so far as the water-absorbent polymer particles are not broken under it. If the particles are broken, then the broken pieces will peel off from fibers and will drop from the final products, absorbent articles. If so, in addition, when the composite has swollen, the water-absorbed gel will drop from the fibers and move somewhere to detract from the quality of the absorbent articles.

When the composition is heated in the step of compressing it, the heating temperature may be up to the melting point of the fibers used. If the composition is heated at a temperature higher than the melting point, then the fibers will fuse to form a network structure and it will interfere with the function of the composite.

When the compression is effected under moisture, the composition is generally moisturized with water vapor. Depending on the moisturizing condition, the density of the composition may be increased and the fixation of fibers to the water-absorbent polymer particles may be improved.

2. Opening of Water-absorbent Polymer Composite Composition

Since the constitutive components of the water-absorbent polymer composite composition are independent of each other, the composition is readily openable like the masses of the composite A mentioned above. For opening it, the methods mentioned hereinabove in the section of opening fibers are also employable in the same manner. Preferred are devices and conditions not damaging the water-absorbent polymer particles through any mechanical shock applied thereto.

IV. Method of Measurement and Evaluation

1. Fibers

1) Contact Angle to Water (1) The fibers to be analyzed were dissolved or dispersed in a solvent capable of dissolving or dispersing them to give a solution or dispersion having a concentration of from 1 to 10% by weight.

(2) The solution or dispersion was spread thin on a laboratory dish, the solvent was gently evaporated away in dry air at room temperature, and this was thus fully dried to give a thin film on the dish.

(3) A drop of distilled water at 25° C. was applied to the air-facing surface of the film, and the contact angle of the water drop to the film surface was measured with an automatic contact angle meter, Kyowa Kaimen Kagaku's Model CA-V.

2) Space Density:

On the presumption that the fibers fed into a reactor could move downward along with the air stream fed thereinto as a multi-phase flow with the fibers, the amount of the fibers staying in the reaction field was calculated, and this was divided by the volume of the overall reaction field to give the space density of the fibers in the reaction field.

2. Droplets

1) Droplet Diameter

The average particle size dp and the monomer concentration Cm of the water-absorbent polymer particles that constitute the water-absorbent polymer composite to be analyzed were measured according to the method 3.2) described hereinunder, and the droplet diameter was derived from them, according to the following equation:

Droplet diameter $dd=dp/(Cm)^{1/3}$

2) Space Density

On the presumption that the droplets could drop downward in the reaction field and that the downward jetting speed of the droplets through the nozzle could be the initial speed thereof, the amount of the droplets staying in the reaction field was calculated, and this was divided by the volume of the overall reaction field to give the space density of the droplets in the reaction field.

3) Degree of Polymerization (Degree of Polymerization in Contact Site with Fibers)

(1) A beaker with methanol (about 150 g) therein was set in such a manner that the level of methanol was the same as the feeding level of the fibers. Droplets of a reaction mixture were formed in a gas phase to begin polymerization, and the droplets (about 1 g) under polymerization were led into methanol in the beaker.

(2) The monomer amount in methanol was measured through liquid chromatography.

(3) The polymer in methanol was dried at 130° C. under reduced pressure for 3 hours, and its weight was measured.

(4) From the data, the degree of polymerization was derived according to the equation mentioned below, in which Mp indicates the polymer weight and Mm indicates the monomer weight.

Degree of polymerization $(\%)=[Mp/(Mn+Mp)]\times 100$

3. Water-absorbent Polymer Composite

1) Identification of Structure of Water-absorbent Polymer Composite (1) The water-absorbent polymer composite can be confirmed by the observation with an SEM at a power of 20 to 20,000 magnifications if the structure of the composite of such that the fibers were partially wrapped in the polymer and were partially exposed outside the polymer. And also adhesion status of the fibers can be confirmed by the same observation.

(2) Furthermore the water-absorbent polymer composite was continuously cut with a precision cutter such as a microtome, and its cross section was observed with an SEM at a power of 20 to 20,000 magnifications. It was confirmed by the observation if the fibers were partially wrapped in the polymer and were partially exposed outside the polymer.

2) Average Particle Diameter of Water-absorbent Polymer Particles

An optical microscopic picture of the water-absorbent polymer composite to be analyzed was taken, on which 100 water-absorbent polymer particles constituting the composite were randomly sampled out (these were all nearly spherical) and their diameter was measured. The individual data were averaged to give an average diameter of the sample analyzed.

3) Dry Weight Ratio of Water-absorbent Polymer Composites:

About 1 g of the water-absorbent polymer composite to be analyzed was observed with an optical microscope. Thus observed, the sample was grouped into composite A, composite B and composite C. Every composite was weighed with a precision balance, and the dry weight ratio of the constitutive composites was calculated.

4) Dry Weight Ratio of Bonding Fibers to Water-absorbent Polymer in Composite

Analyzed in the previous item 3) in point of the dry weight ratio of the constitutive polymer composite segments, the water-absorbent polymer composite to be analyzed was processed in a chemical capable of selectively dissolving the water-absorbent polymer alone in the composite to thereby isolate the fibers. Then, the weight of the fibers was measured.

Concretely, for the water-absorbent polymer composite A:
(1) The weight of the composite A determined in the item 3) was represented by Wc. The composite A was put into a sealable 50-ml glass bottle, and a solution prepared by dissolving 0.03 g of L-ascorbic acid in 25 g of distilled water was added to swell it. In that condition, this was kept at 40° C. for 24 hours.
(2) Next, through filter paper that had been dried under reduced pressure at 80° C. for 3 hours to have a constant weight, the contents of the glass bottle were filtered under suction by the use of an aspirator at an ultimate vacuum of 10 to 25 mmHg, and the fibers remaining on the filter paper were well washed with water, dried at 100° C. for 5 hours and then accurately weighed. Thus measured, the weight was represented by Wf.
(3) According to the following equation, the dry weight ratio of the bonding fibers to the water-absorbent polymer constituting the water-absorbent polymer composite A was obtained.

Dry Weight Ratio of bonding fibers to water-absorbent polymer=$Wf/(Wc-Wf)$

5) Evaluation of Opening Property
(1) About 5 g of the water-absorbent polymer composite was put between a pair of hand carders (22 cm×12.5 cm) manufactured by Ash Ford, and processed five times by hand for worsted.
(2) Based on the easiness in processing for worsted and on the condition of the broken water-absorbent polymer particles, the sample was evaluated in 3 ranks as follows:

A: The sample was easily processed for worsted, and few water-absorbent polymer particles were damaged after the treatment.

B: There was some resistance to the treatment for worsted. After processed for worsted, some water-absorbent polymer particles were damaged.

C: Treatment for worsted was impossible because of too high resistance; but if the sample was forcedly treated against the resistance, the water-absorbent polymer particles were seriously damaged.

6) Water Retention
(1) A necessary amount of physiological saline (aqueous 0.9 wt. % sodium chloride solution) was prepared.
(2) The ratio of the bonding fibers to the water-absorbent polymer in the water-absorbent polymer composite to be analyzed was determined according to the same method as in the above item 3.3), and the water-absorbent polymer composite was collected so that the weight of the water-absorbent polymer in the composite was about 1 g, and the composite was weighed. Its weight was W1. In addition, the weight (W2) of the fibers in the water-absorbent polymer composite was calculated from the ratio of the fibers to the water-absorbent polymer.
(3) This water-absorbent polymer composite was placed in a 250-mesh nylon bag (20 cm×10 cm), and dipped in 500 ml of physiological saline at room temperature for 30 minutes.
(4) Next, the nylon bag was pulled up, hung for 15 minutes to drain it, and then centrifuged in a centrifuge under 90 G for 90 seconds for dewatering.
(5) After thus dewatered, the nylon bag with the water-absorbent composite therein was weighed, and its weight was W3.
(6) The same fibers as those used in producing the composite were placed in a 250-mesh nylon bag (20 cm×10 cm) of the same type as above. The weight of the fibers put into the bag was the same (W2) as that of the fibers in the composite analyzed herein. The nylon bag with the fibers therein was dipped in 500 ml of physiological saline at room temperature for 30 minutes.
(7) Next, the nylon bag was pulled up, hung for 15 minutes to drain it, and then centrifuged in the centrifuge under 90 G for 90 seconds for dewatering. After thus dewatered, the nylon bag with the fibers therein was weighed, and its weight was W4.
(8) The water retention S of the composite for physiological saline was calculated according to the equation mentioned below. In this, W1 to W3 were all by the unit of gram (g).

Water Retention, $S=[(W3-W4)/(W1-W2)]$

7) Water-absorbing Capacity Under Pressure

The water-absorbing capacity under pressure (AUL) is an index of the water-absorbing capacity of a water-absorbent material with a load. This can be measured as follows (see FIG. 1).
(1) The water-absorbent polymer composite was collected so that the weight of the water-absorbent polymer in the composite was about 0.16 g, and the composite was weighed. A cylinder 12 with a metal gauze 11 (metal gauze #100, inner diameter 25.4 mmφ) was weighed. Thus weighed, the weight of the water-absorbing polymer composite was Sd (g), and that of the cylinder was Td (g).
(2) 25 g of artificial urine were placed in a laboratory dish 13 (100 mmφ).
(3) The water-absorbent polymer composite was uniformly fed into the metal gauze-fitted cylinder.
(4) A weight 14 (100 g) was placed on the water-absorbent polymer composite. There should be neither resistance nor friction between the weight 14 and the cylinder 12.
(5) The cylinder 12 with the water-absorbent polymer composite therein was gently dipped in the artificial urine in the dish 13, with its metal gauze facing downward.
(6) In that condition, the composite was kept absorbing the urine for 1 hour.
(7) The cylinder 12 was gently removed from the dish 13.
(8) The cylinder 12 was gently placed on a filter paper (#424), and the excess liquid around its bottom with the metal gauze fitted thereto was wiped off.
(9) The weight 14 was removed and the water-absorbent polymer composite having adhered to the weight was transferred to the cylinder.
(10) The cylinder 12 was weighed. This is the weight of the cylinder 12 having absorbed the liquid, Tw (g).
(11) The weight of the sample having absorbed the liquid, Sw (g) was obtained according to the following equation.

$Sw=Tw-(Sd+Td)$

(12) The water-absorbing capacity under pressure of the fibers alone that were the same as those used in the water-absorbent polymer composite was measured. For this, the fibers were processed according to the same process as in 1) to 11), in which the weight of the fibers in 2), Nd (g) was measured, and the weight of the wetted fibers in 11), Nw (g) that corresponds to the liquid absorption of the fibers alone was measured.

(13) The water-absorbing capacity under pressure was obtained according to the following equation.

Water absorption $A$ (g)=$Sw$−$Nw$

Water-absorbing capacity under pressure ($AUL$) (g/g) =$A$/($Sd$−$Nd$).

4. High-density Water-absorbent Polymer Composite Composition

1) Production of High-density Water-absorbent Polymer Composite Composition

Based on the weight ratio of the water-absorbent polymer composites obtained in the above item 3 and on the dry weight ratio of the bonding fibers to the water-absorbent polymer constituting each water-absorbent polymer composite also obtained in the above item 3, water-absorbent polymer composites and free fibers were mixed in such a controlled ratio that the weight of the water-absorbent polymers and the dry weight ratio of the fibers (bonding fibers+ free fibers) to the water-absorbent polymer could be predetermined values.

For example, when a mixed water-absorbent polymer composite x [g/m$^2$] that comprises the composites A, B and C in which the dry weight ratio of A, B and C is a, b and c, respectively, (a+b+c=1) and the dry weight ratio of the fibers constituting the composites A, B and C is α, β and γ, respectively, is combined with free fibers y [g/m$^2$] to give a high-density water-absorbent polymer composite composition in which the weight of the water-absorbent polymer is P [g/m$^2$] and the dry weight ratio of the free fibers to the water-absorbent polymer is F [w/w], then it satisfies the following relational equations:

$\{a(1-\alpha)+b(1-\beta)+c(1-\gamma)\}x=P$ [g/m$^2$], and $y/[\{a(1-\alpha)+b(1-\beta)+c(1-\gamma)\}x]=F$ [w/w].

Accordingly, when a, b, c, α, β, γ, P and F are given in these equations, then x and y can be obtained from the equations. In these, P=300 g/m$^2$ (constant value).

The mixture was uniformly sheeted on a stainless plate to have an area of 40 cm×10 cm, and another stainless plate was placed on it. A load of 0.6 MPa was applied to both sides of the resulting sandwich structure, and this was left as such for 20 minutes. The pressure was released, and a high-density water-absorbent polymer composite composition was thus produced.

The high-density water-absorbent polymer composite composition produced according to the process as above was evaluated and measured according to the methods mentioned below.

2) Thickness

Figure 2:
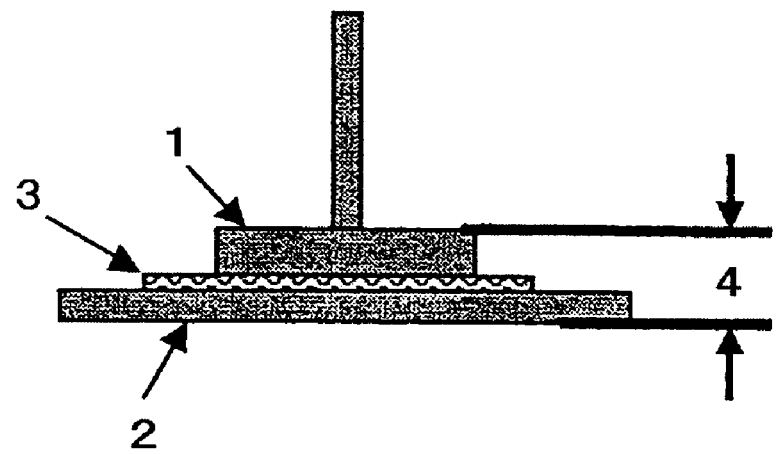
FIG. 2 is a schematic sectional view showing an instrument for measuring thickness of the sample.

The high-density water-absorbent polymer composite composition was cut into a piece of 5 cm×5 cm. Thickness was measured in conformity to Japanese Industrial Standard (JIS) I-1096 (FIG. 2).

(1) An adapter 1 of 30 mm diameter was fitted to a rheometer (Model NRM-2003J by FUDOH), and a sample stand 2 was set to elevate at a speed of 2 cm/min and stop when a pressure of 0.2 psi was given thereto.

(2) A sample 3 was placed on the stand 2, and the stand 2 was moved up.

(3) After the stand 2 received a pressure of 0.2 psi and stopped elevating, the distance 4 between the upper face of the adapter 1 and the lower face of the sample stand 2 was measured with a slide caliper.

(4) Five samples were measured and their data were averaged. With no sample on the stand 2, the blank measurement was carried out in the same manner.

(5) The thickness of the sample was obtained according to the following equation:

Thickness (mm)=sample value measured (mm)− blank value measured (mm)

3) Bulk Density Measurement

The high-density water-absorbent polymer composite composition was cut into a piece of 5 cm×5 cm. The weight of the sample was measured and the bulk density thereof was obtained according to the equation mentioned below. Five samples were measured and their data were averaged.

Bulk Density (g/cm$^3$)=[(sample weight, g)/(sample thickness, cm)×sample area, cm$^2$)]

4) Pliability

Figure 3:
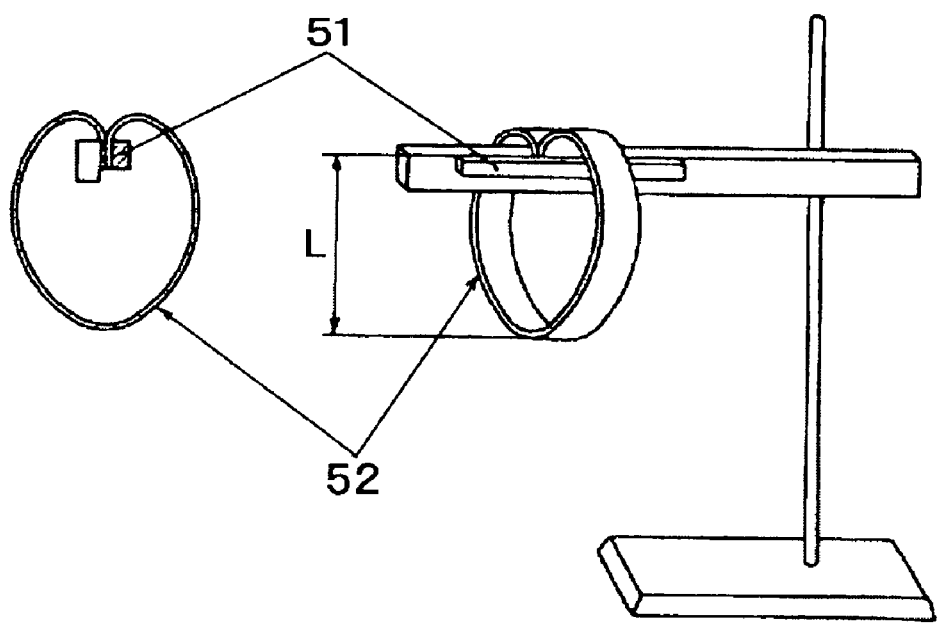
FIG. 3 is a schematic view showing an instrument for measuring pliability by the heart loop method.

The water-absorbent polymer composite was cut into a piece of 2 cm×25 cm. This was kept at a temperature of 25° C. and at a humidity of 50% for one full day, and then its pliability was measured according to the heart loop method of JIS L-1096. The method is used for testing relatively soft fabrics, and this is illustrated in FIG. 3. Concretely, the sample 52 was fitted to the gripper 51 of the horizontal bar so that it formed a heart loop as in FIG. 3. The effective length of the sample was 20 cm. After left as such for 1 minute, the distance L (mm) between the top of the horizontal bar and the loop was measured. The value L indicates the pliability of the sample. Five samples were tested, and their data were averaged.

5) Recovery Evaluation

The high-density water-absorbent polymer composite composition was cut into apiece of 5 cm×5 cm. The sample was compressed at the load of 1 MPa for 10 min. According to the method for measuring the thickness in 4.2), thickness of the sample was measured just after the compression and after storage at a temperature of 25° C. and at a humidity of 50% for 30 days. The recovery of the sample was calculated according to the following equation. Five samples were tested, and their data were averaged.

Recovery after Compression (%)={[(thickness after kept compressed for 30 days, mm)−(thickness just after compressed, mm)]/(thickness just after compressed, mm)}×100

5. Absorbent Articles (Fabrication of Water-absorbent Article)

Figure 4:
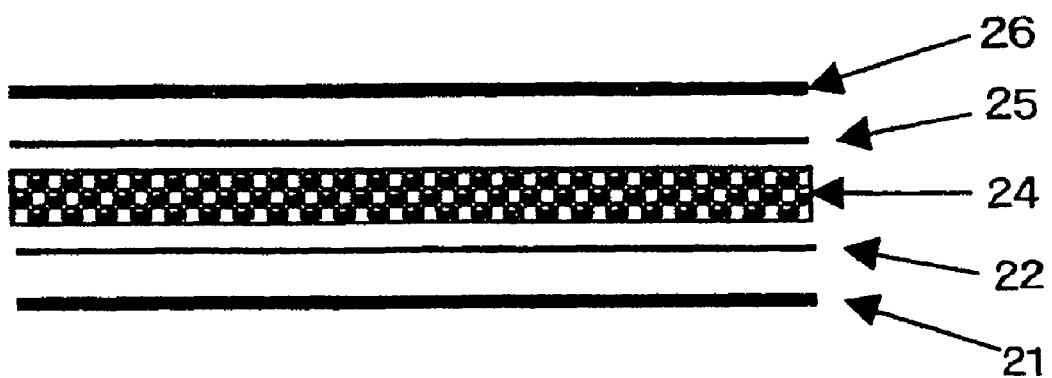
FIG. 4 is a schematic sectional view showing the structure of the water-absorbent article.

A high-density water-absorbent polymer composite composition was utilized in the following method to fabricate a water-absorbent article:

(1) Tissue 22 (14 g/m$^2$), high-density water-absorbent polymer composite composition 24 (containing 300 g/m$^2$ of a water-absorbent polymer, and having a size of 10 cm×40 cm), tissue 25 (14 g/m$^2$), and water-pervious polyester fiber nonwoven fabric 26 (23 g/m$^2$) were piled up in that order on a water-impervious polyethylene sheet 21 (18 g/m$^2$), as in FIG. 4. This was sandwiched between a pair of stainless sheets, and kept under a load of 0.6 MPa for 20 minutes so as to compact the layers.

(2) This was released from the pressure, and the four edges of the thus-fabricated water-absorbent article were heat-sealed.
(3) The heat-sealed edges were then trimmed to obtain a water-absorbent article having a size of about 10 cm×about 40 cm.

The obtained water-absorbent article was measured and evaluated as follows:

1) Water-absorbent Polymer Dropout

The water-absorbent article was cut into a piece having a size of 10 cm×10 cm (its four edges are all open), and its weight was measured. The overall weight of the water-absorbent polymer in the sample was calculated based on the weight percent of the water-absorbent polymer in the composite. Using a tape, the piece of the water-absorbent article was fixed in the center of a standard sieve (40) defined in JIS Z8801 (its inner frame dimension was as follows: the inner diameter is 150 mm, the depth is 45 mm, the pore size is 8 mesh).

Figure 5:
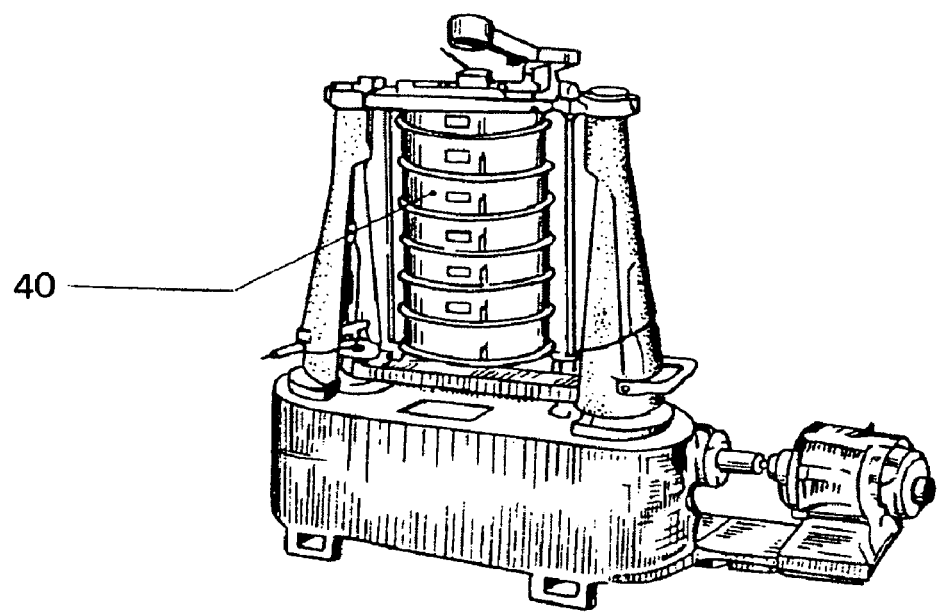
FIG. 5 is a schematic view showing the ro-tap shaker.

(2) This was set in a ro-tap shaker, Tokyo Shinohara Seisakusho's Model SS-S-228, as in drawing (FIG. 5) of JIS Z8815.

(3) The water-absorbent article was fixed only in the uppermost stage, and the shaker was driven at a number of impacts of 165/min, and at a number of revolutions of 290 rpm. After having shaken for 60 minutes in that condition, the weight of the water-absorbent polymer particles having dropped off from the water-absorbent article was measured. The water-absorbent polymer dropout was obtained according to the following equation.

Water-absorbent polymer dropout (%)=[(weight of the dropped water-absorbent polymer, g)/ (weight of the overall water-absorbent polymer before shaken, g)]×100.

2) Gel Dropout

Figure 6:
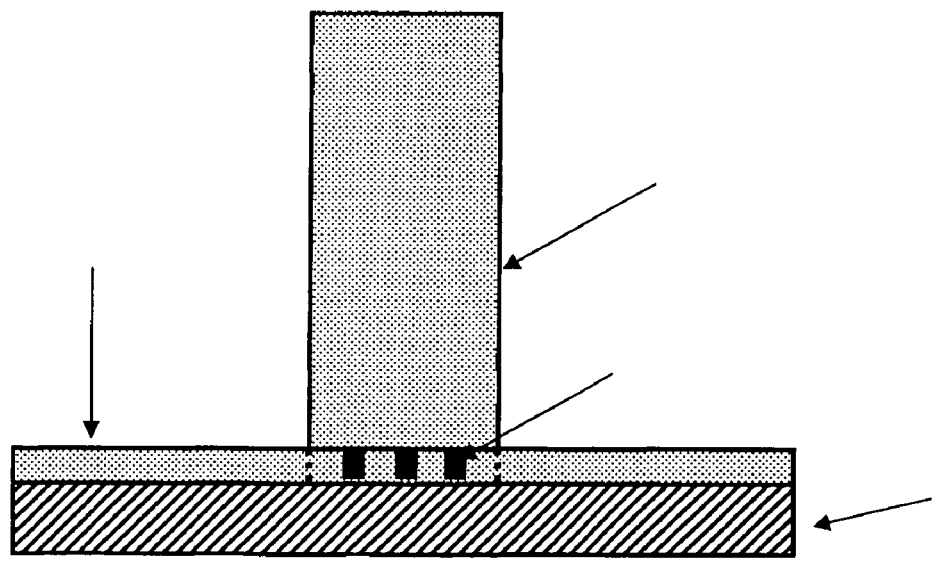
FIG. 6 is a schematic sectional view showing an instrument for measuring gel dropout.

The water-absorbent article was repeatedly rubbed, whereupon the water-absorbent gel dropout from the article was measured as follows:

(1) The article 31 was placed on a flat and smooth bed, and an acrylic plate 34 (100×100×10 mm, overall weight, 150 g) having, in its center, a cylinder 32 having an inner diameter of 40 mm with its top being opened was set as in FIG. 6. In the area surrounded by the cylinder 32 of the acrylic plate 34, 7 through-holes 33 each having a diameter of 5 mm were formed nearly at regular intervals.

(2) 150 ml of artificial urine, of which the composition is mentioned below, was poured into the cylinder so that the water-absorbent article was kept absorbing it. After the article had fully absorbed the liquid, it was further kept at room temperature for 30 minutes.

Figure 7:
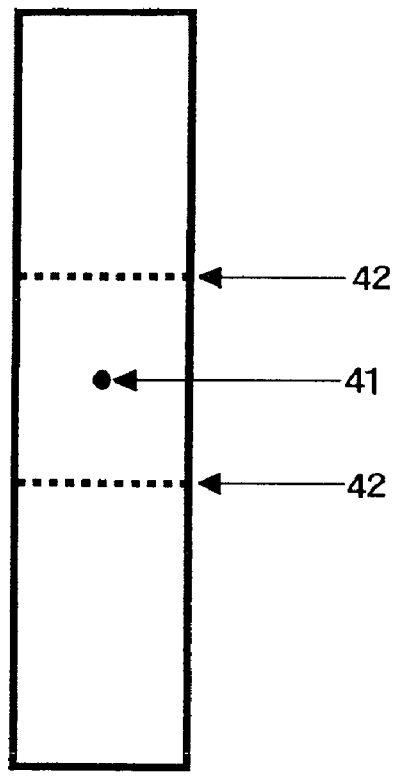
FIG. 7 illustrates the cutting lines in the sample for measurement of gel dropout.

(3) Then, this was cut along the cutting lines 42 that are 5 cm separated from the center 41, as in FIG. 7. The weight of the thus-cut piece was measured.

(4) After thus measured, it was placed on the center of an acrylic plate of 20 cm×20 cm. A weight (3 kg) having the same bottom area (10 cm×10 cm) as the area of the sample piece was placed on the sample piece in accordance with the shape of the sample piece so that the sample piece did not jet out of the weight.

(5) Thus combined, the sample was set in a shaker (Iuchi Seieido's Model MS-1) in such a manner that the cut edge of the sample was perpendicular to the running direction of the shaker. With that, the shaker was driven to a shaking width of 50 mm and at a number of revolution of 80 rpm/min, for 30 minutes.

(6) After thus shaken, the sample was released from the weight, and the weight of the water-absorbent gel having dropped off from the sample was measured. The gel dropout was calculated according to the following equation.

Gel dropout (%)=[(amount of dropped gel, g)/(total amount of gel before the test, g)]×100

6. Others

The artificial urine used in the measurement of 5.1) water-absorbent polymer dropout and 5.2) gel dropout has the following composition:

| Urea | 1.94 wt % |
| Sodium chloride | 0.80 wt % |
| Calcium chloride | 0.06 wt % |
| Magnesium sulfate | 0.11 wt % |
| Distilled water | 97.09% |

The invention is described more concretely with reference to the following Examples, Comparative Example and Test Example. The materials, the amounts used, the ratios, the processes and the process orders in the following Examples may be changed or modified in any desired manner so long as such change does not deviate from the sprit of the invention. Accordingly, the scope of the invention should not be construed in a limitative way based on the following examples.

EXAMPLE 1

100 parts by weight of acrylic acid was neutralized by adding 133.3 parts by weight of a 25 wt % aqueous solution of sodium hydroxide and 3.3 parts by weight of distilled water. This solution, an aqueous solution of partially neutralized acrylic acid, had a monomer concentration of 50 wt % and a degree of neutralization of 60 mol %. Then a solution A was prepared by adding 0.14 parts by weight of N,N'-methylenebisacrylamide as a crosslinking agent, and 4.55 parts by weight of a 31 wt % aqueous solution of hydrogen peroxide as an oxidizing agent, to 100 parts by weight of an aqueous solution of partially neutralized acrylic acid.

Separately, a solution B was prepared by adding 0.14 parts by weight of N,N'-methylenebisacrylamide as a crosslinking agent, and 0.57 parts by weight of L-ascorbic acid as a reducing agent, to 100 parts by weight of the same aqueous solution of partially neutralized acrylic acid as prepared in solution A.

Figure 8:
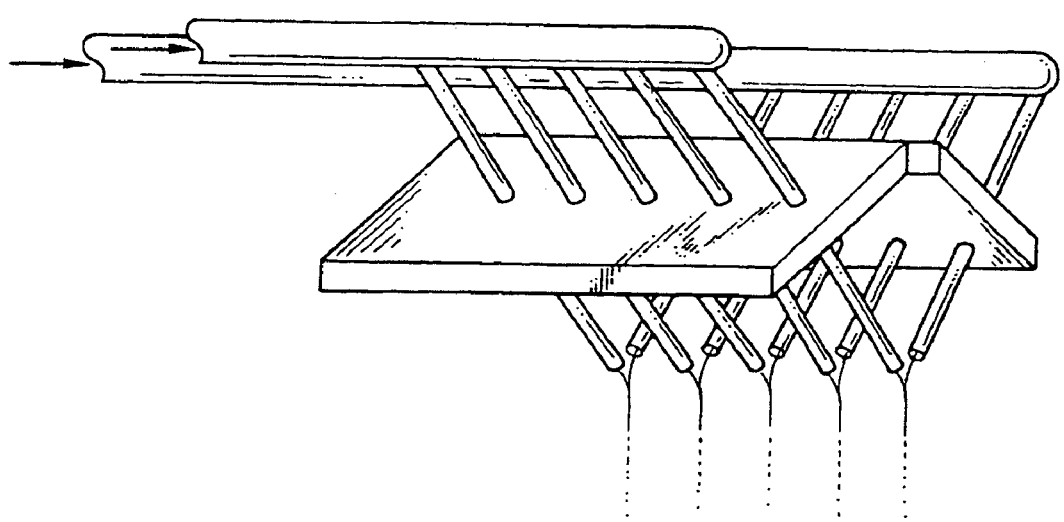
FIG. 8 is a schematic view showing a nozzle structure used for preparation of the water-absorbent polymer composite.

The solution A and the solution B, thus prepared, were mixed through the nozzles shown in FIG. 8. Each nozzle in FIG. 8 has an inner diameter of 0.13 mm, and five nozzles for each solution are disposed at intervals of 1 cm. The crossing angle at which the solution A and the solution B having impinged through the nozzles cross each other is 30 degrees, and the distance between the nozzle tips is 4 mm. Both the solution A and the solution B were heated at 40° C., and fed into the nozzles via pumps so that the jet-out rate of each solution could be 5 m/sec.

The solution A and the solution B met together just after left from the nozzle tips of the respective nozzle pairs, and formed a liquid column of about 10 mm long, and thereafter they fell down in the gas phase (air, 50° C.) while forming droplets under polymerization. The space density of the droplets in the reactor, which is estimated from the space volume of the reactor, the amount of the monomer fed into the reactor and the falling speed of the droplets, is 2 g/m³.

On the other hand, opened fibers were fed with air (fibers/air=1/100) into the reactor through a first supply port and a second supply port disposed at 0.8 m and 1.6 m below the nozzle tips, respectively. The air in the mixed-phase flow was at room temperature and the linear speed of the mixed-phase flow was 10 m/sec. The monomer conversions at 0.8 m and 1.6 m below the nozzle tips were 15% and 40%, respectively. The fibers used were pulp fibers having a fiber diameter of 2.2 decitex, a length of 2.5 mm, and their contact angle with water is 0°. The feed rate of the fibers was 11.5 g/min for each port. The space density of the fibers responsible for the reaction, which is estimated from the space volume of the reactor, the amount of the fibers fed into the reactor, and the falling speed of the fibers, is 8 g/m³.

The droplets collided with the fibers in the gas phase and formed a water-absorbent polymer composite precursor. This was collected as a deposit on the belt conveyor set at 3 m below the nozzle tips. A mesh belt ran on the belt conveyor. The air was aspirated by a blower under the mesh so that the difference between the pressure above the mesh and the pressure below the mesh was 1,000 Pa. The collected material was sieved to remove free fibers which had not contacted the water-absorbent polymer, to obtain a product.

Figure 9:
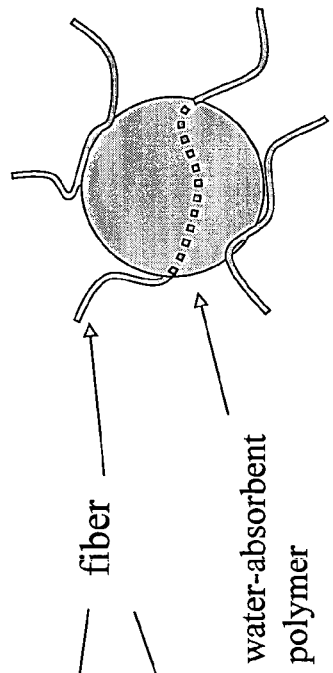
FIG. 9 is a sketch and SEM pictures (101 and 102) of the materials obtained in Example 1.
Figure 9:
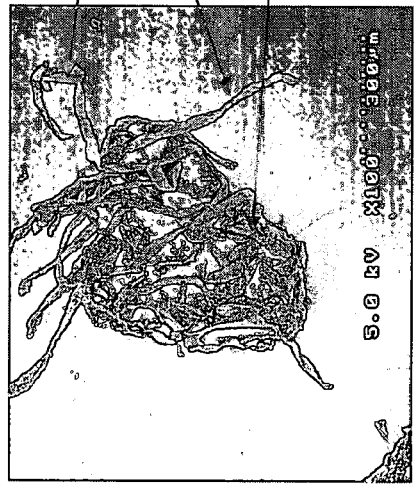
Figure 9:
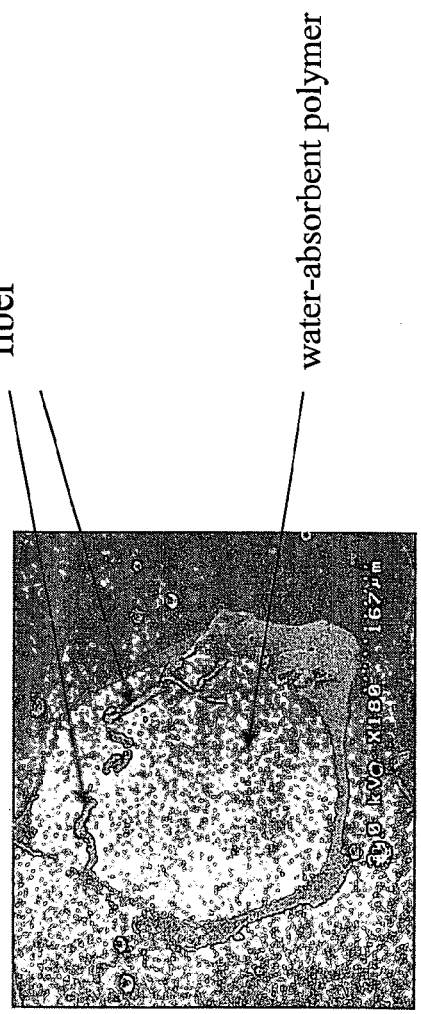

Microscopic observation confirmed that the product was water-absorbent polymer composites comprising a water-absorbent polymer particle and two or more fibers. The particle had a substantially spherical shape. At least one of the two or more fibers was partially wrapped in the polymer particle and partially exposed to outside the particle, and at least one of the two or more fibers was unwrapped in the polymer particle and partially adhered to a surface of the polymer particle. See 101 and 102 in FIG. 9.

EXAMPLE 2

Figure 10:
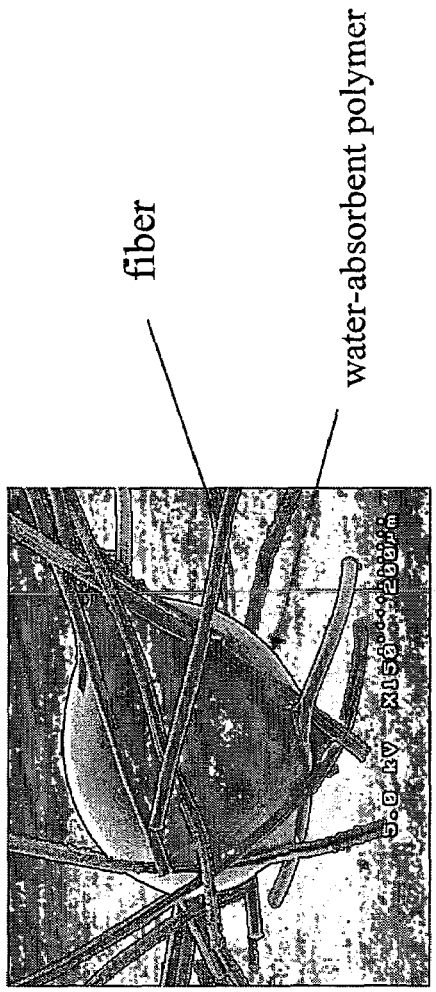
FIG. 10 is SEM pictures (103 and 104) of the materials obtained in Example 2.
Figure 10:
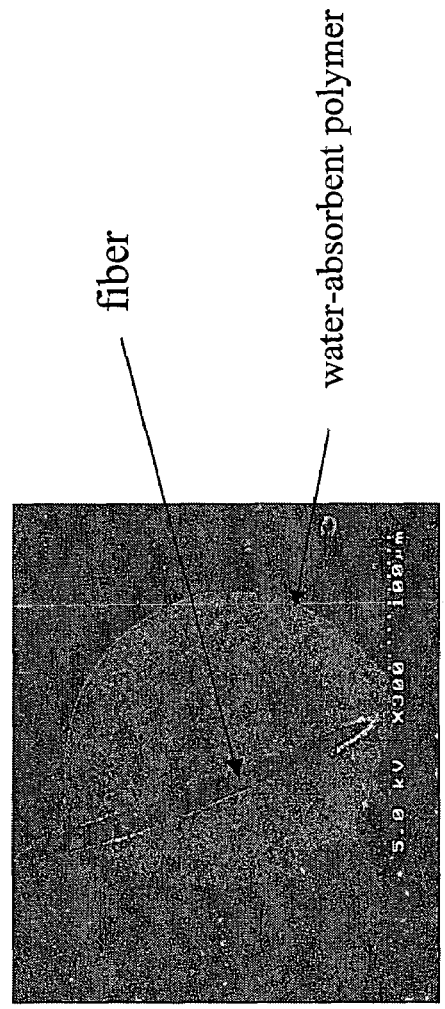

A product was produced in the same manner as in Example 1, except that polyethylene terephthalate (PET) fibers having a fiber diameter of 1.7 decitex, a length of 0.9 mm and a contact angle with water of 80° were used in place of the pulp fibers. It was confirmed that the product was water-absorbent polymer composites having a similar structure to those described in Example 1. See 103 and 104 in FIG. 10.

EXAMPLE 3

Figure 11:
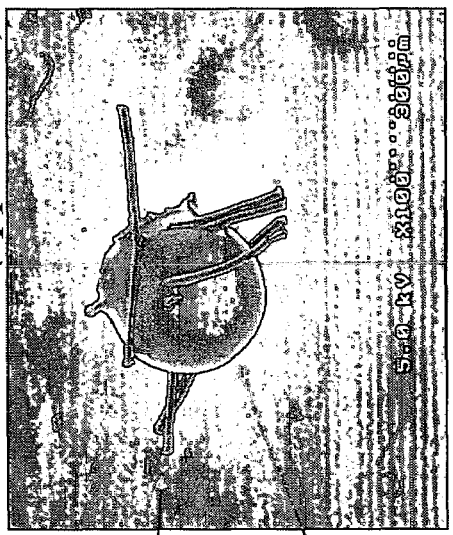
FIG. 11 is SEM pictures (105 and 106) of the materials obtained in Example 3.
Figure 11:
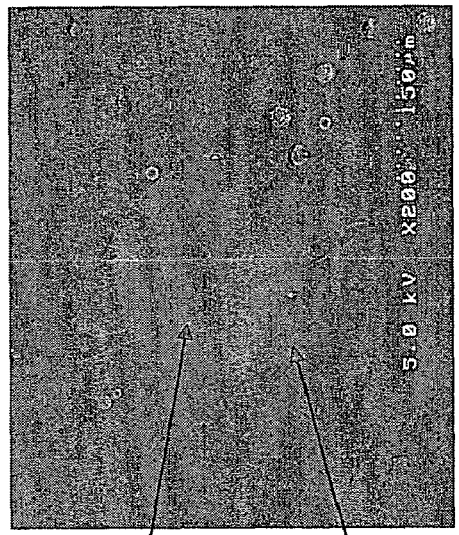

A product was produced in the same manner as in Example 1, except that nylon fibers having a fiber diameter of 1.7 decitex, a length of 0.9 mm and a contact angle with water of 50° were used in place of the pulp fibers. It was confirmed that the product was water-absorbent polymer composites having a similar structure to those described in Example 1. See 105 and 106 in FIG. 11.

EXAMPLE 4

Figure 12:
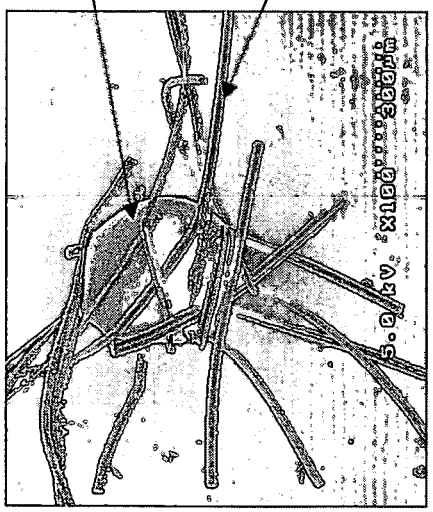
FIG. 12 is SEM pictures (107 and 108) of the materials obtained in Example 4.
Figure 12:
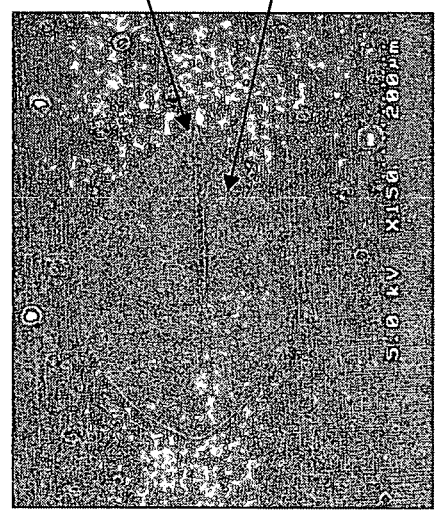

A product was produced in the same manner as in Example 1, except that a fiber mixture of nylon (contact angle with water of 50°)/rayon (contact angle with water of 0°), (nylon/rayon=1/1 by weight) having a fiber diameter of 1.7 decitex and a length of 0.9 mm was used in place of the pulp fibers. It was confirmed that the product was water-absorbent polymer composites having a similar structure to those described in Example 1. See 107 and 108 in FIG. 12.

EXAMPLE 5

Figure 13:
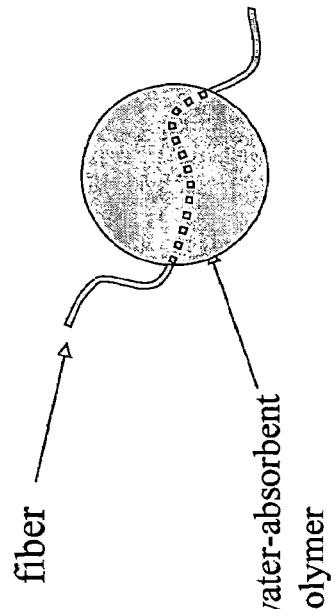
FIG. 13 is a sketch and SEM pictures (109 and 110) of the materials obtained in Example 5.
Figure 13:
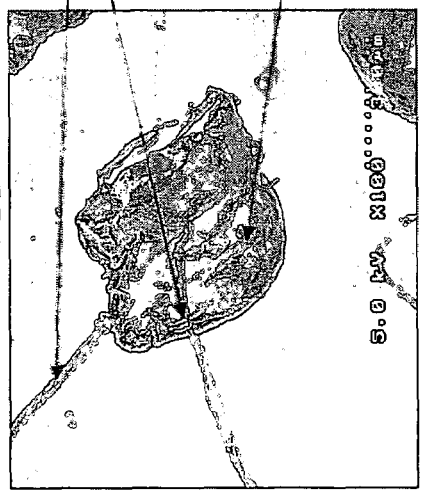
Figure 13:
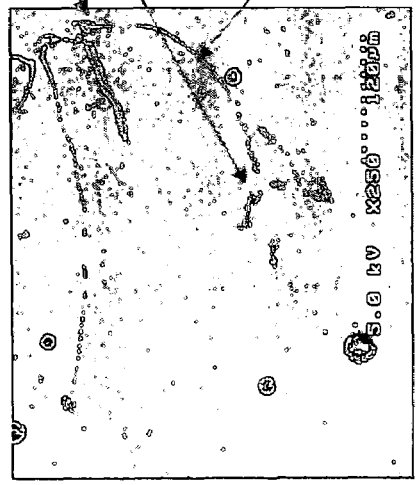

A product was produced in the same manner as in Example 1, except that the fibers were fed from only the supply port disposed at 0.8 m below the nozzle tips. Microscopic observation showed that the product was a composition containing the following two kinds of water-absorbent polymer composites:
1) Water-absorbent polymer composite having the same structure as described in Example 1.
2) Water-absorbent polymer composite of substantially spherical shape comprising one water-absorbent polymer particle and one or more fibers, wherein one or more said fibers are partially wrapped in the polymer particle and partially exposed to outside the particle, and none of said fibers are adhered to a surface of the polymer particles. See sketch, 109 and 110 in FIG. 13.

It was also confirmed by microscopic observation that the weight ratio of the composite 1) to the product was 0.3.

EXAMPLE 6

Figure 14:
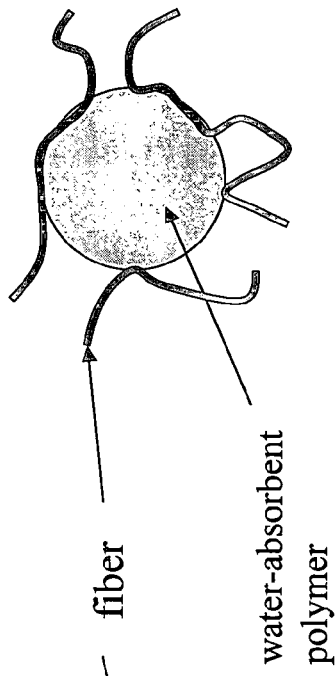
FIG. 14 is a sketch and SEM pictures (111 and 112) of the materials obtained in Example 6.
Figure 14:
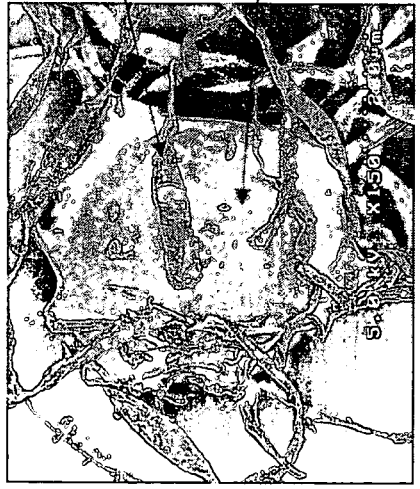
Figure 14:
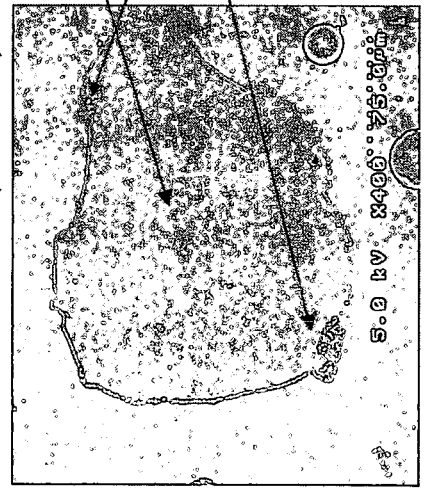

A product was produced in the same manner as in Example 1, except that the fibers were fed from only the supply port disposed at 1.6 m below the nozzle tips. Microscopic observation showed that the product was a composition containing the following two kinds of water-absorbent polymer composites:
1) Water-absorbent polymer composite having the same structure as described in Example 1.
2) Water-absorbent polymer composite of substantially spherical shape comprising one water-absorbent polymer particle and one or more fibers, wherein one or more said fibers are partially adhered to a surface of the polymer particles, and none of said fibers are partially wrapped in the polymer particles (see sketch, 111 and 112 in FIG. 14)

It was also confirmed by microscopic observation that the weight ratio of the composite 1) to the product was 0.2.

EXAMPLE 7

47.5 parts by weight of the composition obtained in Example 5, 47.5 parts by weight of the composition obtained in Example 6 and 5 parts by weight of the same fibers as those used in Example 1 were uniformly mixed by the use of a moving blade-type blender to obtain a product. The product was observed with a microscope, and it was found that the composition comprised the following three types of water-absorbent polymer composites and three types of fibers.
1) Water-absorbent polymer composite having the same structure as that in Example 1.
2) Water-absorbent polymer composite of substantially spherical shape comprising one water-absorbent polymer particle and one or more fibers, wherein one or more said fibers are partially wrapped in the polymer particle and partially exposed to outside the particle, and none of said fibers are adhered to a surface of the polymer particles.
3) Water-absorbent polymer composite of substantially spherical shape comprising one water-absorbent polymer particle and one or more fibers, wherein one or more said fibers are partially adhered to a surface of the polymer particles, and none of said fibers are partially wrapped in the polymer particles.
4) Fibers neither wrapped in nor adhered to the water-absorbent polymer.

It was also confirmed by microscopic observation that the weight ratio of the composite 1) to the product was 0.24.

EXAMPLE 8

A product was produced in the same manner as in Example 1, except that polytetrafluoroethylene (PTFE) fibers having a fiber diameter of 1.7 decitex, a length of 0.9 mm and a contact angle with water of 108° were used in place of the pulp fibers. It was confirmed that the product was water-absorbent polymer composites having a similar structure to those described in Example 1.

COMPARATIVE EXAMPLE 1

A water-absorbent polymer composite composition was produced in the same manner as known in the art referred in JP-A 63-63723.

In a 200-ml beaker, 45.0 g of acrylic acid and 1.5 g of distilled water were placed, and the mixture was neutralized with 60.0 g of a 25% aqueous solution of sodium hydroxide to prepare a partially-neutralized acrylic acid monomer (having a monomer concentration of 50 wt % and a degree of neutralization of 60 mol %) with the temperature being maintained at 35° C. or lower by cooling. In the monomer solution, 41.9 mg of N,N'-methylenebisacrylamide and 0.31 g of L-ascorbic acid were dissolved. A 300-ml stainless beaker was completely sealed up with a polyester sheet at its mouth, and the cover sheet was holed. A rubber tube was inserted into the hole, via which the inside atmosphere of the beaker was fully purged with nitrogen. The aqueous solution of the monomers was poured into the stainless beaker, and the beaker was then dipped in a water bath at 50° C. With stirring, 0.84 g of aqueous 30% hydrogen peroxide was added thereto, and the monomer was polymerized. After about 1 minute, the mixture showed a highest temperature of 110° C. This was kept dipped in the water bath at 50° C. for 2 hours, and then cooled to 20° C. The process gave a water-containing, water-absorbent polymer. 70 g of the water-containing, water-absorbent polymer (the net weight of the water-absorbent polymer alone is 35 g) was mixed with 200 g of water and 10 g of opened pulp that is the same as used in Example 1 and a contact angle with water of 0° in a screw-rotary mixer for about 2 hours, then dried in a drier under reduced pressure at 100° C. for 8 hours, and further ground in a moving blade-type grinder to sieve and separate free fibers to obtain a water-absorbent polymer composite composition.

Figure 15:
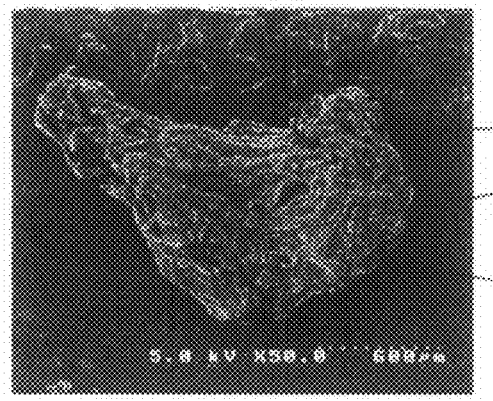
FIG. 15 is a sketch and SEM pictures (113 and 114) of the materials obtained in Comparative Example 1.
Figure 15:
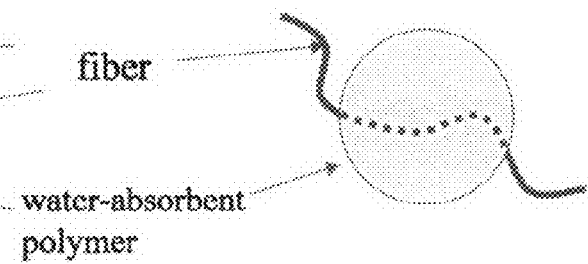
Figure 15:
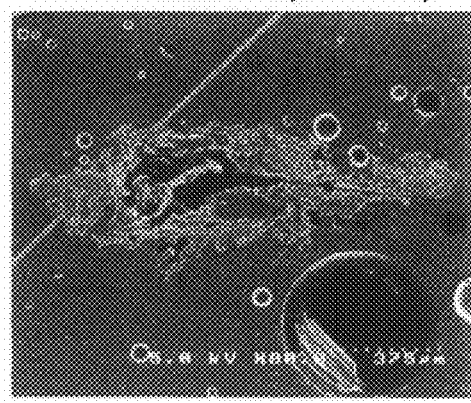

The structure of the product was observed with a microscope, which confirmed that the fibers therein were partially wrapped in the water-absorbent polymer. In the structure, however, the fibers were not wrapped in the polymer particles and were not partially adhered to the surfaces of the polymer particles (graphic view, 113 and 114 in FIG. 15).

COMPARATIVE EXAMPLE 2

A water-absorbent polymer composite composition was produced in the same manner as known in the art referred to in JP-A 11-93073.

125 parts by weight of an aqueous 80 wt. % acrylic acid solution and 133 parts by weight of an aqueous 30 wt. % sodium hydroxide solution were mixed to prepare an aqueous solution of a partially-neutralized acrylic acid having a degree of neutralization of 72 mol % and a concentration of 47% by weight. To the aqueous, partially-neutralized acrylic acid solution, added was a solution that had been prepared by dissolving 0.04 parts by weight of a crosslinking agent, N,N'-methylenebisacrylamide and 0.3 parts by weight of an initiator, 2,2'-azobis(2-amidinopropane) dihydrochloride in 13 parts by weight of distilled water. With that, this was degassed while purged with nitrogen to prepare an aqueous monomer solution.

In place of the nozzle used in Example 1, herein used was a one-pack spray nozzle. Through the nozzle, the monomer solution was fed into a reactor using a pump. The solution temperature was kept at 25° C., and the flow rate was 40 ml/min.

While polymerized, the monomer solution dropped down as liquid drops in a vapor phase (air, 25° C.). The space density of the liquid drops in the reactor was 3 g/m$^3$, estimated from the space volume of the reactor, the amount of the monomer fed into the reactor and the dropping speed of the liquid drops.

On the other hand, opened fibers were fed into the reactor as a mixed phase flow with air (fibers:air=1:100) through a feed mouth disposed at 0.8 m below the nozzle tip. In this stage, the temperature of the air in the mixed phase flow was 25° C., and the linear velocity of the flow was 10 m/sec. The conversion at 0.8 m below the nozzle tip was smaller than 1%. The fibers used were PET fibers having a fiber diameter of 1.7 dtex, a fiber length of 0.9 mm, and a contact angle to water of 90°. The supply amount of the fibers was 11.5 g/min. The space density of the fibers in the reaction site was 8 g/m$^3$, estimated from the space volume of the reaction site, the supply amount of the fibers and the dropping speed of the fibers.

The droplets collided with the fibers in the gas phase and formed a water-absorbent polymer composite precursor. This was collected as a deposit on the belt conveyor set at 3 m below the nozzle tips. A mesh belt ran on the belt conveyor. The air was aspirated by a blower under the mesh so that the difference between the pressure above the mesh and the pressure below the mesh was 1,000 Pa. The deposit was recovered and put into an oven at 80° C., in which the aqueous monomer solution adhering to the deposit was polymerized for 30 minutes, and then processed with hot air at 140° C. to obtain a water-absorbent polymer composite.

Further, the recovered matter was sieved, and this was tried to remove the free fibers. In this, however, the water-absorbent polymer served as an adhesive to bond the fibers, and there were found substantially no free fibers therein. In that manner, a product comprising a water-absorbent polymer and fibers was obtained.

Figure 16:
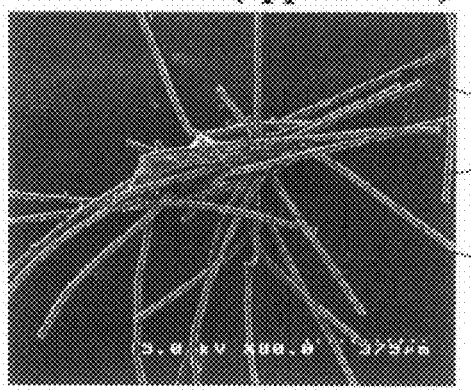
FIG. 16 is a sketch and SEM pictures (115 and 116) of the materials obtained in Comparative Example 2.
Figure 16:
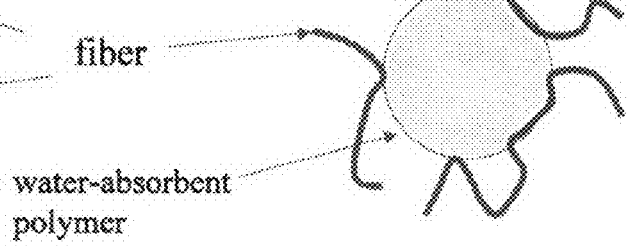
Figure 16:
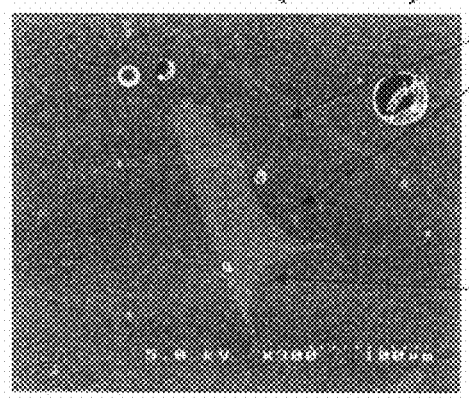

This product was observed with a microscope, which confirmed that a part of the fibers therein were adhered to the surfaces of the polymer particles in the structure of the composition. However, no structure was found in which a part of the fibers were wrapped in the water-absorbent polymer (graphic view, 115 and 116 in FIG. 16).

TEST EXAMPLE

Structure, average particle diameter of the water-absorbent polymer, dry weight ratio of fibers to water-absorbent polymer in composite A, opening property, water retention, and water-absorbing capacity under pressure were determined in the water-absorbent polymer composites and their compositions produced in Examples 1 to 8 and Comparative Examples 1 and 2.

Using the water-absorbent polymer composites produced in Examples 1 to 8 and Comparative Examples 1 and 2, water-absorbent polymer composite compositions were produced. Before they were further processed for increasing their density, the weight ratio of the composites and the free fibers, and the dry weight ratio of the free fibers and the water-absorbent polymer were determined. It is believed that the ratios do not change even after the subsequent compression treatment. The high-density water-absorbent polymer composite compositions that were obtained through the compression treatment of the water-absorbent polymer composite compositions were analyzed in point of the thickness, the bulk density, the stiffness and flexibility, and the recovery thereof.

In addition, the high-density water-absorbent polymer composite compositions were formed into absorbent articles, and the water-absorbent polymer dropout and the gel dropout from the articles were determined.

The result of each measurement and evaluation is summarized in Table 1.

The water-absorbent polymer composites of Comparative Examples 1 and 2 produced pulverized fiber pieces during opening step.

TABLE 1

|  |  |  |  | Ex. 1 | Ex. 2 | Ex. 3 | Ex. 4 | Ex. 5 |
|---|---|---|---|---|---|---|---|---|
| water-absorbent polymer composite and its composition | binding fiber | material | | pulp | PET | nylon | nylon/rayon | pulp |
| | | average fiber length | [mm] | 2.5 | 0.9 | 0.9 | 0.9 | 2.5 |
| | | average fiber diameter | [dtex] | 2.2 | 1.7 | 1.7 | 1.7 | 2.2 |
| | | contact angle of fiber to water | [°] | 0 | 80 | 50 | 50/0 | 0 |
| | | space density | [g/m³] | 8 | 8 | 8 | 8 | 8 |
| | droplet | diameter of droplet | [μm] | 500 | 500 | 500 | 500 | 500 |
| | | space density | [g/m³] | 2 | 2 | 2 | 2 | 2 |
| | supply port | distance from the nozzle tip | [m] | 0.8/1.6 | 0.8/1.6 | 0.8/1.6 | 0.8/1.6 | 0.8 |
| | | polymerization degree | [%] | 15/40 | 15/40 | 15/40 | 15/40 | 15 |
| | measurement and evaluation | average particle size of water-absorbing polymer | [μm] | 400 | 400 | 400 | 400 | 400 |
| | | dry wt. ratio of free fiber to water-absorbent polymer in composite A | [w/w] | 10/90 | 10/90 | 10/90 | 10/90 | 5/95 |
| | | opening property | | ○ | ○ | ○ | ○ | ○ |
| | | water retention | [g/g] | 33 | 33 | 33 | 33 | 33 |
| | | water-absorbing capacity under pressure | [g/g] | 23 | 23 | 23 | 23 | 23 |
| high-density water-absorbent polymer composite composition | Component | wt. ratio of composite A | [wt %] | 100 | 100 | 100 | 100 | 30 |
| | | wt. ratio of composite B | [wt %] | 0 | 0 | 0 | 0 | 70 |
| | | wt. ratio of composite C | [wt %] | 0 | 0 | 0 | 0 | 0 |
| | | wt. ratio of free fiber | [wt %] | 0 | 0 | 0 | 0 | 0 |
| | | dry wt ratio of free fiber to water-absorbent polymer | [w/w] | 0:100 | 0:100 | 0:100 | 0:100 | 0:100 |
| | free fibers | average fiber length | [mm] | — | — | — | — | — |
| | measurement and evaluation | thickness | [mm] | 0.8 | 1.5 | 1.5 | 1.5 | 0.8 |
| | | bulk density | [g/cm³] | 0.42 | 0.22 | 0.22 | 0.22 | 0.39 |
| | | pliability | [cm] | 8.5 | 7.5 | 7.5 | 7.5 | 7.5 |
| | | recovery | [%] | 11 | 20 | 20 | 20 | 11 |
| water-absorbent article | measurement and evaluation | water-absorbent polymer dropout | [%] | 0.9 | 1.0 | 1.0 | 0.9 | 1.5 |
| | | gel dropout | [%] | 1.8 | 2.0 | 3.0 | 2.0 | 1.8 |

|  |  |  |  | Ex. 6 | Ex. 7 | Ex. 8 | Comp. 1 | Comp. 2 |
|---|---|---|---|---|---|---|---|---|
| water-absorbent polymer composite and its composition | binding fiber | material | | pulp | pulp | PTFE | pulp | PET |
| | | average fiber length | [mm] | 2.5 | 2.5 | 0.9 | 2.5 | 0.9 |
| | | average fiber diameter | [dtex] | 2.2 | 2.2 | 1.7 | 2.2 | 1.7 |
| | | contact angle of fiber to water | [°] | 0 | 0 | 108 | 0 | 80 |
| | | space density | [g/m³] | 5 | — | 8 | — | 8 |
| | droplet | diameter of droplet | [μm] | 500 | — | 500 | — | 250 |
| | | space density | [g/m³] | 2 | — | 2 | — | 3 |
| | supply port | distance from the nozzle tip | [m] | 1.6 | — | 0.8/1.6 | — | 0.8 |
| | | polymerization degree | [%] | 40 | — | 15/40 | — | <1 |
| | measurement and evaluation | average particle size of water-absorbing polymer | [μm] | 400 | 400 | 400 | 600 | 200 |
| | | dry wt. ratio of free fiber to water-absorbent polymer in composite A | [w/w] | 5/95 | 5/95 | 10/90 | 10/90 | 5/95 |
| | | opening property | | ○ | ○ | ○ | X | X |
| | | water retention | [g/g] | 33 | 33 | 33 | 28 | 27 |
| | | water-absorbing capacity under pressure | [g/g] | 23 | 23 | 23 | 15 | 15 |
| high-density water-absorbent polymer composite composition | Component | wt. ratio of composite A | [wt %] | 20 | 24 | 100 | 0 | 0 |
| | | wt. ratio of composite B | [wt %] | 0 | 33 | 0 | 100 | 0 |
| | | wt. ratio of composite C | [wt %] | 80 | 38 | 0 | 0 | 100 |
| | | wt. ratio of free fiber | [wt %] | 0 | 5 | 0 | 0 | 0 |
| | | dry wt ratio of free fiber to water-absorbent polymer | [w/w] | 0:100 | 5:95 | 0:100 | 0:100 | 0:100 |
| | free fibers | average fiber length | [mm] | — | 2.5 | — | — | — |
| | measurement and evaluation | thickness | [mm] | 0.8 | 0.8 | 1.5 | 0.8 | 2.0 |
| | | bulk density | [g/cm³] | 0.39 | 0.39 | 0.22 | 0.42 | 0.16 |
| | | pliability | [cm] | 8.5 | 8.0 | 8.0 | 7.5 | 7.5 |
| | | recovery | [%] | 11 | 13 | 18 | 20 | 20 |
| water-absorbent article | measurement and evaluation | water-absorbent polymer dropout | [%] | 0.9 | 0.9 | 4.0 | 0.9 | 22 |
| | | gel dropout | [%] | 2.5 | 1.9 | 4.0 | 1.9 | 17 |

INDUSTRIAL APPLICABILITY OF THE INVENTION

The water-absorbent polymer composite and its composition of the invention are favorable for producing sanitary goods such as paper diapers, sanitary napkins, and other water-absorbent articles such as industrial materials. Particularly the water-absorbent polymer composite and its composition of the invention can be applied and available for the techniques utilized in the area of water-absorbent sheets described as in JP-A 63-267370, 63-10667, 63-295251, 63-270801, 63-294716, 64-64602, 1-231940, 1-243927, 2-30522, 2-153731, 3-21385, 4-133728 and 11-156118.

The present disclosure relates to the subject matter contained in PCT/JP2004/005396 filed on Apr. 15, 2004, which is expressly incorporated herein by reference in its entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A water-absorbent polymer composite comprising a water-absorbent polymer particle and two or more fibers, wherein said polymer particle has a substantially spherical shape, at least one of said two or more fibers is partially wrapped in the polymer particle and partially exposed to outside the particle, and at least one of said two or more fibers is unwrapped in the polymer particle and partially adhered to a surface of the polymer particle.

2. The water-absorbent polymer composite according to claim 1, wherein a dry weight ratio of said fibers to said polymer particle is in the range of 1:1 to 1:1,000,000.

3. The water-absorbent polymer composite according to claim 1, wherein said polymer particle has an average particle size of 50 to 1,000 micrometers.

4. The water-absorbent polymer composite according to claim 1, wherein said fibers have an average fiber length of 50 to 50,000 micrometers.

5. The water-absorbent polymer composite according to claim 1, wherein said fibers have an average fiber diameter of 0.1 to 500 decitex.

6. The water-absorbent polymer composite according to claim 1, wherein at least one of said two or more fibers has a contact angle against water of 0 to 60 degree.

7. The water-absorbent polymer composite according to claim 6, wherein said fiber is cellulose.

8. The water-absorbent polymer composite according to claim 6, wherein said fiber is pulp.

9. The water-absorbent polymer composite according to claim 1, wherein said water-absorbent polymer is a crosslinked polymer of an unsaturated carboxylic acid.

10. The water-absorbent polymer composite according to claim 1, wherein said water-absorbent polymer is a crosslinked polymer of a partially-neutralized acrylic acid.

11. A water-absorbent composite composition comprising the water-absorbent polymer composite according to claim 1.

12. The water-absorbent composite composition according to claim 11, which further comprises a water-absorbent polymer composite comprising one or more additional water-absorbent polymer particles and one or more additional fibers, wherein said additional polymer particles have a substantially spherical shape, at least one of said additional fibers is partially wrapped in the additional polymer particle and partially exposed to outside the particle, and none of said fibers are adhered to a surface of the additional polymer particles.

13. The water-absorbent composite composition according to claim 11, which further comprises a water-absorbent polymer composite comprising one or more additional water-absorbent polymer particles and one or more additional fibers, wherein said additional polymer particles have a substantially spherical shape, at least one of said additional fibers is partially adhered to a surface of the additional polymer particles, and none of said additional fibers are partially wrapped in the additional polymer particles.

14. The water-absorbent composite composition according to claim 11, which further comprises one or more fibers that are neither wrapped in nor adhered to the water-absorbent polymer particles contained in the water-absorbent composite composition.

15. The water-absorbent composite composition according to claim 14, wherein a dry weight ratio of said fibers that are neither wrapped in nor adhered to the water-absorbent polymer particles to the water-absorbent polymer particles contained in the water-absorbent composite composition is in the range of 90:10 to 5:95.

16. The water-absorbent composite composition according to claim 14, wherein said fibers that are neither wrapped in nor adhered to the water-absorbent polymer particles contained in the water-absorbent composite composition have an average fiber length of 50 to 100,000 micrometers.

17. The water-absorbent composite composition according to claim 11, which has a bulk density of 0.15 to 0.85 g/cm$^3$.

18. The water-absorbent composite composition according to claim 11, which can be opened.

19. A water-absorbent composite composition comprising the water-absorbent polymer composite according to claim 1 in a weight fraction of 0.1 or more.

* * * * *